United States Patent [19]

Torgerson et al.

[11] Patent Number: 5,980,878
[45] Date of Patent: *Nov. 9, 1999

[54] THERMOPLASTIC ELASTOMERIC COPOLYMERS AND HAIR AND SKIN CARE COMPOSITIONS CONTAINING THE SAME

[75] Inventors: Peter Marte Torgerson, Washington Court House; Sanjeev Midha, Blue Ash, both of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/904,741

[22] Filed: Aug. 1, 1997

Related U.S. Application Data

[63] Continuation of application No. 08/440,852, May 15, 1995, abandoned, which is a continuation of application No. 08/259,070, Jun. 20, 1994, abandoned, which is a continuation-in-part of application No. 08/257,962, Jun. 16, 1994, abandoned, which is a continuation-in-part of application No. 08/231,955, Apr. 21, 1994, abandoned, which is a continuation of application No. 08/086,605, Jul. 1, 1993, abandoned.

[51] Int. Cl.[6] .................. A61K 31/785; A61K 7/075; C02F 226/06
[52] U.S. Cl. ................ 424/70.122; 424/70.12; 526/265; 526/279
[58] Field of Search ........................... 424/70.11

[56] References Cited

U.S. PATENT DOCUMENTS

| | | | |
|---|---|---|---|
| 3,786,116 | 1/1974 | Milkovich | 525/276 |
| 4,176,862 | 12/1979 | Maximovich et al. | 525/96 |
| 4,507,280 | 3/1985 | Pohl et al. | 424/70.17 |
| 4,663,158 | 5/1987 | Wolfram | 424/70.16 |
| 4,693,935 | 9/1987 | Mazurek | 428/352 |
| 5,106,609 | 4/1992 | Bolich, Jr. et al. | 424/70.12 |
| 5,153,273 | 10/1992 | Kobayashi | 525/412 |
| 5,262,087 | 11/1993 | Tachibana et al. | 252/309 |

FOREIGN PATENT DOCUMENTS

| | | | |
|---|---|---|---|
| 0412704 | 2/1991 | European Pat. Off. | |
| 3028202 | 2/1991 | Japan | C08F 2/32 |
| 4359914 | 12/1992 | Japan | C08F 299/08 |
| WO 91/15186 | 10/1991 | WIPO | A61K 7/08 |
| WO 92/09644 | 6/1992 | WIPO | C08F 299/00 |

OTHER PUBLICATIONS

S. I. Klenin, et al., "Molecular Structure . . . ", Polymer Science, vol. 34, No. 5, May 1992, pp. 380–383.

A. Maruyama et al., "Synthesis and Characterization of Polyamine Graft Copolymers . . . ", Makromol. Chem., vol. 187, No. 8, pp. 1895–1906, Aug. 13, 1986.

S. Sosnowski et al., "Anionic Living Polymerization . . . ", Makromol. Chem., vol. 188, No. 6, pp. 1347–1354, Jun. 26., 1986.

*Primary Examiner*—Peter F. Kulkosky
*Attorney, Agent, or Firm*—Stephen T. Murphy; Loretta J. Henderson

[57] ABSTRACT

The present invention relates to water or alcohol soluble or dispersible thermoplastic elastomeric copolymers and to cosmetic and pharmaceutical compositions containing these copolymers. This invention especially relates to copolymers useful for hair styling purposes, and to hair styling compositions containing these copolymers. This invention further relates to copolymers useful for providing cosmetic and pharmaceutical compositions for topical application to the skin. These topical skin care compositions are useful for delivereing and/or transdermally transporting active ingredients to or thorugh the skin.

18 Claims, No Drawings

THERMOPLASTIC ELASTOMERIC COPOLYMERS AND HAIR AND SKIN CARE COMPOSITIONS CONTAINING THE SAME

This is a file-wrapper continuation of application Ser. No. 08/440,852, filed on May 15, 1995, abandoned which is a file-wrapper continuation of application Ser. No. 08/259,070, filed on Jun. 20, 1994 (abandoned), which is a continuation-in-part of application Ser. No. 08/257,962, filed on Jun. 16, 1994, abandoned which is a contuation-in-part of application Ser. No. 08/231,955, filed on Apr. 21, 1994 (abandoned), which is a continuation of application Ser. No. 08/086,605, filed on Jul. 1, 1993 (abandoned).

TECHNICAL FIELD

The present invention relates to water or alcohol soluble or dispersible thermoplastic elastomeric copolymers and to cosmetic and pharmaceutical compositions containing these copolymers. These copolymers are useful for hair setting and styling purposes. A particularly useful application for these copolymers is in hair spray and mousse compositions. This invention further relates to copolymers useful for incorporating into cosmetic and pharmaceutical compositions for topical application to the skin. Skin care compositions containing these copolymers are useful for delivering and/or transdermally transporting a wide variety of active ingredients to and/or through the skin.

BACKGROUND OF THE INVENTION

In the hair care area, the desire to have hair retain a particular style or shape is widely held. Such style retention is generally accomplished by either of two routes: permanent chemical alteration of the hair fiber or temporary alteration of hair style or shape. A temporary alteration is one which can be removed by water or by shampooing. Temporary style alteration has generally been accomplished by application of a composition to dampened hair after shampooing and/or conditioning and prior to drying and/or styling. Products in the form of mousses, gels, lotions, or sprays are most commonly used for this purpose. Once the desired style is achieved, spray products are commonly used to help retain the style. These various hair care products utilize a variety of gums and resins for providing styling and retention. However, the gums and resins currently used tend to feel either too sticky or too stiff upon the hair. Also, these gums and resins do not wash out as easily as desired. Therefore, the need exists for improved styling and style retention materials which provide a strong, lasting, hold without being either too stiff or too sticky, and yet which are easily removed by shampooing. Furthermore, because most hair care styling compositions are water and/or alcohol based, it is necessary that these materials have good solubility or dispersibility in these bases.

Thermoplastic elastomeric copolymers are well known. These copolymers combine thermoplastic properties, which give them solubility and strength, with rubber-like elastic properties, which give them flexibility and shape retention. However, despite these highly desirable properties, most thermoplastic elastomeric copolymers are generally insoluble or poorly soluble in water and/or alcohol systems and would not be suitable in hair care compositions. Therefore, thermoplastic elastomeric copolymers having good water and/or alcohol solubility would be useful for developing improved hair care compositions.

In the present invention new classes of thermoplastic elastomeric copolymers have been developed which have the desired flexibility, strength, and elastic properties and yet are readily soluble and/or dispersible in water and/or alcohol systems. Furthermore, these materials provide hair care compositions which leave the hair feeling natural, i.e. not stiff.

In addition to the hair care benefits provided by these copolymers, it has been found that these materials are also useful for incorporation into a wide variety of cosmetic and pharmaceutical compositions for topical application to the skin. These copolymers provide topical compositions which are more easily and uniformly spread upon the skin, which feel good upon the skin, and yet which are highly substantive. Furthermore, these copolymers are useful for enhancing the penetration of a wide variety of cosmetic and pharmaceutical actives into the skin, or alternatively, through the skin for systemic delivery.

It is an object of the present invention to provide novel, water and/or alcohol soluble and/or dispersible thermoplastic elastomeric copolymers.

It is another object of the present invention to provide novel thermoplastic elastomeric copolymers useful in hair care compositions.

It is another object of the present invention to provide novel hair care compositions having improved styling and/or hold properties and having improved aesthetics.

It is another object of the present invention to provide novel thermoplastic elastomeric copolymers useful in topical skin care cosmetic and pharmaceutical compositions.

It is another object of the present invention to provide novel topical cosmetic and pharmaceutical compositions useful for delivering a wide variety of cosmetic materials and pharmaceutical actives to and/or through the skin.

These and other objects will become readily apparent from the detailed description which follows.

SUMMARY OF THE INVENTION

The present invention relates to a water or alcohol soluble or dispersible thermoplastic elastomeric copolymer having a backbone and two or more polymeric pendant side chains, said copolymer formed from the copolymerization of randomly repeating A and B units wherein said copolymer comprises:

(i) from about 40% to about 90% by weight of said A units, wherein said A units are polymerizable monomer units; and (ii) from about 10% to about 60% by weight of said B units, wherein said B units are hydrophilic macromonomer units copolymerizable with A, whereby said macromonomer units form said pendant polymeric side chains;

wherein said copolymer has a weight average molecular weight greater than about 10,000, and wherein said copolymer exhibits two distinct $T_g$ values, said first $T_g$ corresponding to said backbone and having a value less than about 0° C., and said second $T_g$ corresponding to said side chains and having a value greater than about 25° C.

The present invention also relates to a water or alcohol soluble or dispersible thermoplastic elastomeric copolymer having a backbone and two or more polymeric side chains, said copolymer formed from the copolymerization of randomly repeating A and B units and corresponding to the formula

wherein A is at least one polymerizable monomer unit corresponding to the formula

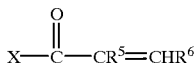

wherein X is selected from the group consisting of —OH, —OM, —OR$^4$, —NH$_2$, —NHR$^4$, and —N(R$^4$)$_2$; M is a cation selected from the group consisting of Na+, K+, Mg++, Ca++, Zn++, NH$_4$+, alkylammonium, dialkylammonium, trialkylammonium, and tetralkylammonium; each R$^4$ is independently selected from the group consisting of H, C$_1$–C$_8$ straight or branched chain alkyl, N,N,-dimethylaminoetpyl, 2-hydroxyethyl, 2-methoxyethyl, and 2-ethoxyethyl; and R$^5$ and R$^6$ are independently selected from the group consisting of H, C$_1$–C$_8$ straight or branched chain alkyl, methoxy, ethoxy, 2-hydroxyethoxy, 2-methoxyethyl, and 2-ethoxyethyl.

B is at least one hydrophilic macromonmer unit copolymerizable with A corresponding to the formula

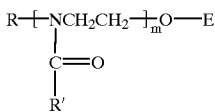

wherein E is an ethylenically unsaturated moiety, copolymerizable with A, selected from the group consisting of vinyl, allyl, acryloyl, methacryloyl, ethacryloyl, 3-vinylbenzoyl, and 4-vinylbenzoyl; R and R' are independently selected from the group consisting of H and C$_1$–C$_8$ straight or branched chain alkyl; m is an integer from about 10 to about 2000; a is an integer of about 100 or greater; and b is an integer of about 2 or greater.

In further embodiments, B is at least one hydrophilic macromonomer unit copolymerizable with A corresponding to the formula

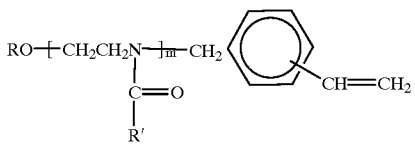

wherein R and R' are independently selected from the group consisting of H and C$_1$–C$_8$ straight or branched chain alkyl; m is an integer from about 10 to about 2000; a is an integer of about 100 or greater; and b is an integer of about 2 or greater.

In further embodiments, B is at least one hydrophilic macromonmer unit copolymerizable with A corresponding to the formula

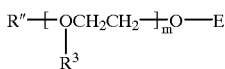

wherein E is an ethylenically unsaturated moiety, copolymerizable with A, selected from the group consisting of vinyl, allyl, acryloyl, methacryloyl, ethacryloyl, 3-vinylbenzoyl, and 4-vinylbenzoyl, and mixtures thereof; R" is selected from the group consisting of C$_1$–C$_{40}$ straight or branched chain alkyl; R$_3$ is selected from the group consisting of H, and C$_1$–C$_8$ straight or branched chain alkyl; m is an integer from about 20 to about 2000; a is an integer of about 100 or greater; and b is an integer of about 2 or greater.

In further embodiments, B is at least one hydrophilic macromonomer unit copolymerizable with A corresponding to the formula

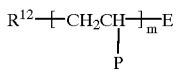

wherein E is an ethylenically unsaturated moiety, copolymerizable with A, selected from the group consisting of vinyl, allyl, acryloyl, methacryloyl, ethacryloyl, 2-vinyl benzyl, 3-vinyl benzyl, 4-vinyl benzyl, and mixtures thereof; R$^{12}$ is selected from the group consisting of hydrogen, C1–6 straight or branched chain alkyl, benzyl, 1-phenyl substituted C2–6 straight or branched chain alkyl, 1,1 -diphenyl substituted C2–6 straight or branched chain alkyl, and mixtures thereof; P is a polar moiety selected from the group consisting of 2-pyridyl, 3-pyridyl, 4-pyridyl, halogen substituted 2-, 3-, or 4-pyridyl, C1–4 alkyl substituted 2-, 3-, or 4-pyridyl, 2-aminophenyl, 3-aminophenyl, 4-aminophenyl, 2-aminomethylphenyl, 3-aminomethylphenyl, 4-aminomethylphenyl, 2-aminoethylphenyl, 3-aminoethylphenyl, and 4-aminoethylphenyl, and pharaceutically acceptagle salts and quaternized derivatives thereof, and mixtures thereof; and m is an integer from about 20 to about 2000.

Infurther embodiments, B is at least one hydrophilic macromonomer unit copolymerizable with A and C corresponding to the formula

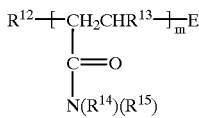

wherein E is an ethylenically unsaturated moiety, copolymerizable with A, selected form the group consisting of vinyl, allyl, acryloyl, methacryloyl, ethacryloyl, 2-vinyl benzyl, 3-vinyl benzyl, 4-vinyl benzyl, and mixtures thereof; R$^{12}$ is selected from the group consisting of hydrogen, C1–C6 straight or branched chain alkyl, benzyl, 1-phenyl substituted C2–6 straight or branched chain alkyl, 1,1-diphenyl substituted C2–6 straight or branched chain alkyl, and mixtures thereof; and R$^{13}$ is selected from the group consisting of H and C1–6 straight or branched chain alkyl, and R$^{14}$, and R$^{15}$ are independently selected form the group consisting of C1–8 straight or branched chain alkyl; and m is is an integer from about 20 to about 2000.

In further embodiments, the present invention relates to hair care compositions, especially hair setting and styling compositions, containing these copolymers.

In further embodiments, the present invention relates to cosmetic and pharmaceutical compositions containing these copolymers for topical application to the skin for the delivery of cosmetic materials and pharmaceutical actives onto, into and/or through the skin.

All percentages and ratios used herein are by weight of the total composition and all measurements made are at 25° C., unless otherwise designated. The invention hereof can comprise, consist of, or consist essentially of, the essential as well as optional ingredients and components described herein.

DETAILED DESCRIPTION OF THE INVENTION

The term "thermoplastic elastomeric copolymer" as used herein means that the copolymer has both thermoplastic and elastomeric properties. The term "thermoplastic elastomeric copolymer" is one familiar to those of ordinary skill in polymer science. By "thermoplastic" is meant that upon heating, the copolymer softens and upon cooling it rehardens; upon being subject to stress it begins to flow and upon removal of stress it stops flowing. By "elastomeric" is meant that the copolymer has an elastic modulus such that the copolymer exhibits a resistance to deformation and has limited extensibility and retraction. In other words, the copolymer tends to recover its size and shape after deformation.

The term "macromonomer" is one familiar to those of ordinary skill in polymer science, and is used to describe a polymeric material containing a polymerizable moiety. A macromonomer is a macromolecular monomer. A macromonomer is essentially a very large type of monomer building block unit which can be used in a polymerization reaction to form polymers with itself, with other monomers, or with other macromonomers.

The term "water or alcohol soluble or dispersible" as used herein means that these copolymers are either freely soluble in or dispersible (as a stable suspension) in at least one of the following solvents, or alternatively, in any combination of one of the following solvents: water, methanol, ethanol, and isopropanol. By "soluble" is meant that the copolymer is soluble in the solvent or solvents at 25° C. at a concentration of at least about 20 mg/mL, more preferably about 50 mg/mL, and most preferably about 100 mg/mL. By "dispersible" is meant that the copolymer forms a stable, uniform suspension (without the addition of further materials such as emulsifiers) when combined with the solvent or solvents at 25° C. at a concentration of at least about 20 mg/mL, more preferably about 50 mg/mL, and most preferably about 100 mg/mL.

Thermoplastic Elastomeric Copolymers

The copolymers of the present invention are characterized in having an elastomeric or flexible backbone and rigid, thermoplastic, hydrophilic side chains. This combination of both elastomeric and thermoplastic moieities in a single copolymer provides the unique and useful properties of these materials. The copolymers of the present invention, can also be referred to as "graft copolymers" because they can be prepared from the copolymerization of monomer units and macromonmer units. In other words, the macromonomer is "grafted" or incorporated into the copolymer.

These copolymers exhibit two distinct immiscible phases. Without being limited by theory, it is believed that the hydrophilic side chains of these copolymers are closely associated with each other, thereby existing in one phase, while the backbone of the copolymer remains in a separate phase. A consequence of this phase immiscibility is that these copolymers exhibit two distinct glass transition temperatures or, "$T_g$'s", for the backbone and the side chains. $T_g$ is a well known term of art in polymer science used to describe the temperature at which a polymer or portion thereof undergoes a transition from a solid or brittle material to a liquid or rubber-like material. Glass transition temperatures can be measured using standard techniques that are well known to the polymer scientist of ordinary skill in the art. One particularly useful technique for determining glass transitions is differential scanning calorimetry (also known as DSC). The glass transition phenomenon in polymers is described in *Introduction to Polymer Science and Technology: An SPE Textbook*, (eds. H. S. Kaufman and J. J. Falcetta), (John wiley & Sons: 1977), which is incorporated by reference herein in its entirety.

The $T_g$ of the backbone of the copolymers herein (i.e. that part of the copolymer not containing the side chains) should be less than about 0° C. Preferably the $T_g$ of the backbone should be from about –10° C. to about –130° C., more preferably from about –20° C. to about –125° C., and most preferably from about –55° C. to about –120° C. The $T_g$ of the side chain of the copolymers (i.e. that part of the copolymer not containing the backbone) is greater than about 20° C. Preferably the $T_g$ of the sidechain should be from about 25° C. to about 200° C., more preferably from about 30° C. to about 175° C., and most preferably from about 35° C. to about 150° C.

Because these copolymers possess two distinct $T_g$'s, these copolymers are useful in hair styling and setting compositions. Without being limited by theory, it is believed that when these copolymers are subjected to temperatures above both $T_g$'s, they are essentially liquid and can provide great flexibility during the styling process (e.g., when curling irons, blow driers, and other heat sources are applied to the hair). Upon cooling of the copolymer to room temperature (e.g. when the heat source is removed from the hair) the copolymer is then at a temperature that is typically between both $T_g$'s, and the copolymer possesses structural rigidity from the macromonomer side chains, and yet has flexibility from the backbones, and can provide a strong, yet flexible, hair hold or style retention.

Furthermore, at skin temperatures, these copolymers would be at a temperature which is essentially between both $T_g$'s. These copolymers can enhance the film forming properties of skin care compositions, and provide benefits shuch as better and more even distribution upon the skin.

The copolymers of the present invention are formed from the copolymerization of randomly repeating A and B units, preferably wherein the A units are selected from at least one polymerizable, ethylenically unsaturated monomer unit, and the B units are selected from at least one hydrophilic macromonomer unit which contains an ethylenically unsaturated moiety which is copolymerizable with A. In typical embodiments of these copolymers, the backbone is primarily derived from the ethylenically unsaturated portion of the A monomer unit and the ethylenically unsaturated portion of the B macromonomer unit. The side chains are derived from the non-copolymerized portions of the macromonomer. The A and B units can be selected from a wide vaiety of structures as long as the limitations of the copolymer are met (e.g., solubility, $T_g$'s, and molecular weights).

The A monomer units of the copolymers of the present invention can comprise from about 40% to about 90%, more preferably from about 50% to about 85%, and most preferably from about 60% to about 80%, by weight, of the copolymers.

The hydrophilic B macromonomer units can comprise from about 10% to about 60%, more preferably from about 15% to about 50%, and most preferably from about 20% to about 40%, by weight of the copolymers.

The copolymers of the present invention have a weight average molecular weight of at least about 10,000. There is no upper limit for molecular weight except that which limits applicability of the invention for practical reasons, such as viscosity, processing, aesthetic characteristics, formulation compatibility, etc. In general, the weight average molecular weight is less than about 5,000,000, more generally less than about 2,500,000, and typically less than about 1,500,000. Preferably, the weight average molecular weight is from about 10,000 to about 5,000,000, more preferably from about 75,000 to about 1,000,000, even more preferably from about 100,000 to about 850,000, and most preferably from about 125,000 to about 750,000.

Alternatively, the copolymers of the present invention can also be represented by the formula

[A]<sub>a</sub>[B]<sub>b</sub> wherein A and B are as described herein, and where a is an integer of about 100 or greater, preferably a is an integer from about 100 to about 3000, more preferably from about 250 to about 2000, and most preferably from about 350 to about 1500, and b is an integer of about 2 or greater, preferably from about 2 to about 50, more preferably from about 2 to about 20, and most preferably from about 2 to about 10. In this formula, it is expressly intended that even though ranges are provided for the subscripts a and b, these subscripts are not intended to strictly limit the polymers herein so long as the physical propoerties of the polymers are achieved. When the copolymers herein are described by the formula disclosed in this paragraph it has been found useful to describe the copolymers by their number average molecule weights. In general, the number average molecular weight is less than about 2,500,000, more generally less than about 1,500,000, and typically less than about 1,000,000. Preferably, the number average molecular weight is from about 15,000 to about 1,000,000, more preferably from about 20,000 to about 500,000, and most preferably from about 25,000 to about 250,000.

By appropriate selection and combination of the particular A and B units and by the choice of specific relative ratios of the units well within the ability of one of ordinary skill in the art, the copolymers can be optimized for various physical properties such as solubility, $T_g$'s, and the like, and for compatibility with other ingredients commonly used in hair care and skin care applications.

When the copolymers of the present invention are incorporated into hair and/or skin care compositions, the copolymers typically comprise from about 0.1% to about 25%, preferably from about 0.5% to about 20%, more preferably from about 1% to about 10%, and most preferably from about 2% to about 5% of the composition, although higher or lower amounts can be used depending upon the particular application.

Monomer "A" Units

The "A" monomer unit is selected from polymerizable monomers, preferably ethylenically unsaturated monomers. Either a single A monomer or combinations of two or more A monomers can be utilized. For example, if two different A monomers are polymerized with a B macromonomer, the resulting copolymer could be described as a terpolymer. In either case, the monomers are selected to meet the requirements of the copolymer. By "polymerizable", as used herein, is meant monomers that can be polymerized using any conventional synthetic techniques. Monomers that are polymerizable using conventional free radical initiated techniques are preferred. The term "ethylenically unsaturated" is used herein to mean monomers that contain at least one polymerizable carbon-carbon double bond (which can be mono-, di-, tri-, or tetra-substituted).

The A monomer units of the copolymers of the present invention can comprise from about 40% to about 90%, more preferably from about 50% to about 85%, and most preferably from about 60% to about 80%, by weight, of the copolymers.

The ethylenically unsaturated A monomer units preferably can be described by the following formula

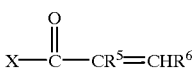

wherein X is selected from the group consisting of —OH, —OM, —OR$^4$, —NH$_2$, —NHR$^4$, and —N(R$^4$)$_2$; M is a cation selected from the group consisting of Na+, K+, Mg++, Ca++, Zn++, NH$_4$+, alkylammonium, dialkylammonium, trialkylammonium, and tetralkylammonium; each R$^4$ is independently selected from the group consisting of H, C$_1$–C$_8$ straight or branched chain alkyl, N,N-dimethylaminoethyl, 2-hydroxyethyl, 2-methoxyethyl, and 2-ethoxyethyl; and R$^5$ and R$^6$ are independently selected from the group consisting of H, C$_1$–C$_8$ straight or branched chain alkyl, methoxy, ethoxy, 2-hydroxyethoxy, 2-methoxyethyl, and 2-ethoxyethyl.

Representative nonlimiting examples of monomers useful herein include acrylic acid and salts, esters, and amides thereof. The salts can be derived from any of the common nontoxic metal, ammonium, or substituted ammonium counter ions. The esters can be derived from C$_{1-40}$ straight chain, C3–40 branched chain, or C3–40 carbocyclic alcohols; from polyhydric alcohols having from about 2 to about 8 carbon atoms and from about 2 to about 8 hydroxy groups (nonlimiting examples of which include ethylene glycol, propylene glycol, butylene glycol, hexylene glycol, glycerin, and 1,2,6-hexanetriol); from amino alcohols (nonlimiting examples of which include aminoethanol, dimethylaminoethanol, and diethylaminoethanol, and their quaternized derivatives); or from alcohol ethers (nonlimiting examples of which include methoxyethanol, and ethoxy ethanol). The amides can be unsubstituted, N-alkyl or N-alkylamino mono-substituted, or N,N-dialkyl or N,N-dialkylamino di-substituted, wherein the alkyl or alkylamino group can be derived from C$_{1-40}$ straight chain, C3–40 branched chain, or C3–40 carbocylic moieties. Additionally, the alkylamino groups can be quaternized. Also useful as monomers are substituted acrylic acids and salts, esters, and amides thereof (wherein the substituents are on the two and three carbon positions of the acrylic acid and are independently selected from the group consisting of C$_{1-4}$ alkyl, —CN, —COOH (e.g., methacrylic acid, ethacrylic acid, and 3-cyano acrylic acid). The salts, esters, and amides of these substituted acrylic acids can be defined as described above for the acrylic acid salts, esters, and amides. Other useful monomers include vinyl and allyl esters of C$_{1-40}$ straight chain, C3–40 branched chain, or C3–40 carbocylic carboxylic acids; vinyl and allyl halides (e.g., vinyl chloride and allyl chloride); vinyl and allyl substituted heterocylic compounds (e.g., vinyl pyrridine and allyl pyridine); vinylidene chloride; and hydrocarbons having at least one carbon-carbon double bond (e.g., styrene, alpha-methylstyrene, t-butylstyrene, butadiene, isoprene, cyclohexadiene, ethylene, propylene, 1-butene, 2-butene, isobutylene, vinyl toluene); and mixtures thereof.

Preferred A monomers useful herein include those selected from the group consisting of acrylic acid, methacrylic acid, ethacrylic acid, methyl acrylate, ethyl acrylate, n-butyl acrylate, iso-butyl acrylate, t-butyl acrylate, 2-ethylhexyl acrylate, decyl acrylate, methyl methacrylate, ethyl methacrylate, n-butyl methacrylate, iso-butyl methacrylate, t-butyl methacrylate, 2-ethylhexyl methacrylate, decyl methacrylate, methyl ethacrylate, ethyl ethacrylate, n-butyl ethacrylate, iso-butyl ethacrylate, t-butyl ethacrylate, 2-ethylhexyl ethacrylate, decyl ethacrylate, 2,3-dihydroxypropyl acrylate, 2,3- dihydroxypropyl methacrylate, 2-hydroxyethyl acrylate, 2-hydroxypropyl acrylate, hydroxypropyl methacrylate, glyceryl monoacrylate, glyceryl monomethacrylate, acrylamide, methacrylamide, ethacrylamide, N-methyl acrylamide, N,N-dimethyl acrylamide, N,N-dimethyl methacrylamide, N-ethylacrylamide, N-isopropyl acrylamide, N-butyl acrylamide, N-t-butyl acrylamide, N,N-di-n-butylacrylamide, N,N-diethylacrylamide, N-octyl acrylamide, N-octadecyl acrylamide, N-phenyl acrylamide, N-methyl methacrylamide, N-ethylmethacrylamide, N-dodecylmethacrylamide, N,N-dimethylaminoethyl acrylamide, quaternized N,N-dimethylaminoethyl acrylamide, N,N-dimethylaminoethyl methacrylamide, quaternized N,N-dimethylaminoethyl methacrylamide, N,N-dimethylaminoethyl acrylate, N,N-dimethylamianoethyl methacrylate, quaternized N,N-dimethylaminoethyl acrylate, quaternized N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, maleic anhydride and its half esters, crotonic acid, itaconic acid, angelic acid, diallyidimethyl ammonium chloride, vinyl pyrrolidone, methyl vinyl ether, methyl vinyl ketone, maleimide, vinyl pyridine, vinyl imidazole, vinyl furan, styrene sulfonate, allyl alcohol, vinyl alcohol, vinyl caprolactam, and mixtures thereof. More preferred A monomers are those selected from the group consisting of methyl acrylate, methyl methacrylate, methyl ethacrylate, ethyl acrylate, ethyl methacrylate, ethyl ethacrylate, n-butyl acrylate, n-butyl methacrylate, n-butyl ethacrylate, 2-ethylhexyl acrylate, 2-ethylhexyl methacrylate, 2-ethylhexyl ethacrylate, N-octyl acrylamide, 2-methoxyethyl acrylate, 2-hydroxyethyl acrylate, N,N-dimethylaminoethyl acrylate, and mixtures thereof.

Most preferred A monomers are those selected from the group consisting of n-butyl acrylate, 2-ethylhexyl acrylate, N-octyl acrylamide, 2-methoxyethyl acrylate, 2-hydroxyethyl acrylate, N,N-dimethylaminoethyl acrylate, and mixtures thereof.

Hydrophilic "B" Macromonomer Units

A macromonomer is a large monomer unit, i.e. a macromolecular monomer, which can be further polymerized with itself, with other conventional monomers, or with other macromonomers. The term "macromonomer" is one that is familiar to the polymer chemist of ordinary skill in the art. The hydrophilic "B" macromonomer units of the present invention are very large monomer building blocks which can be formed from the polymerization of smaller monomer units. The B macromonomers encompass a wide variety of structures and are copolymerizable with the A monomer. Either a single B macromonomer or combinations of two or more B macromonomers can be utilized. In either case, the macromonomers are selected to meet the requirements of the copolymer.

The hydrophilic B macromonomers comprise from about 10% to about 60%, more preferably from about 15% to about 50%, and most preferably from about 20% to about 40%, by weight of the copolymers.

By the term "copolymerizable" as used herein is meant B macromonomers that can be reacted with the A monomer in a polymerization reaction using any conventional synthetic techniques. "Copolymerization" is a term of art used to refer to the simultaneous polymerization of two or more different monomers. In the present invention, B macromonomers that are copolymerizable with A monomers using conventional free radical initiated techniques are preferred. By the term "hydrophilic" as used herein is meant B macromonomers that are soluble in or have an affinity for water and/or other polar, water-soluble solvent materials (e.g., methanol, ethanol, propanol, isopropanol and the like). "Hydrophilic" is also a term of art used to described a substance having a strong tendency to absorb water which results in the swelling, solubilization, or dispersion of the substance in water. Without being limited by theory, the hydrophilic B macromonomer units are believed to contribute to the overall water or alcohol soluble or dispersible properties of the copolymers.

B macromonomers that are useful herein contain an ethylenically unsaturated moiety that is copolymerizable with the A monomer. The term "ethylenically unsaturated" is used herein to mean B macromonomers that contain at least one carbon-carbon double bond (which can be mono-, di-, tri-, or tetra-substituted). Typically, the preferred B macromonomers are those that are endcapped with the ethylenically unsaturated moiety. By "endcapped" as used herein is meant that the ethylenically unsaturated moiety is at or near a terminal position of the macromonomer. However, this definition of "endcapped" is not intended to limit the macromonomer to only those macromonomers which terminate in a carbon-carbon double bond (whether mono-, di-, tri-, or tetra-substituted).

The hydrophilic B macromonomers of the present invention can be synthesized utilizing a variety of standard synthetic procedures familiar to the polymer chemist of ordinary skill in the art. Furthermore, these macromonomers can be synthesized starting from commercially available polymers. Typically the weight average molecular weight of the macromonomer is from about 1000 to about 200,000, more preferably from 1500 to about 30,000, and most preferably from about 2000 to about 25,000.

For example, the hydrophilic B macromonomers can be synthesized by the polymerization (acid, base, free radical, or auto-initiated) of a hydrophilic monomer to form a polymer which is subsequently reacted with or "endcapped" with a structural unit E, containing the ethylenically unsaturated moiety. Alternatively, the B macromonomers can be synthesized starting with commercially available hydrophilic polymers which are "endcapped" with the structural unit E. In yet another alternative, the B macromonomer can be synthesized by starting with the structural unit E, and polymerizing onto it the desired hydrophilic monomer units. It is to be understood that in this third alternative, the ethylenically unsaturated moiety of the E unit is not consumed in the synthesis but its integrity is preserved for subsequent copolymerization of the B macromonomer with the A monomer units. All of the synthetic alternatives are merely illustrative in that any other suitable synthetic procedures can be utilized to prepare the B macromonomers and copolymers of the present invention.

The B macromonomers can be described by the following formula

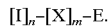

$[I]_n-[X]_m-E$.

X is a hydrophilic monomer unit, and m is an integer from about 10 to about 2000, preferably from about 15 to about 300, and more preferably from about 20 to about 250, so that the macromonomer meets the weight average molecular weight requirements set forth above. Preferred is when X is a hydrophilic monomer unit selected from the group consisting of oxazolines, N-alkyloxazolines, alkylene glycols, N-vinylpyrrolidones, N-allylpyrrolidones, vinylpyridines, allylpyridiens, vinylcaprolactams, allylcaprolactams, vinylimidazoles, allylimidaoles, vinylfurans, allylfurans, vinyltetrahydrofurans, allyltetrahydrofurans, vinaylaminobenzenes, vinylaminomethylbenzenes, vinylaminoethylbenzenes, N,N-dialkylacrylamides, N,N-dialkyl(alkyl)acrylamides, and mixtures thereof. More preferred is wherein X is a monomer unit selected from the group consisting of N-alkyloxazolines, alkylene glycols, vinylpyridines, N,N-dialkylacrylamides, N,N-dialkyl(alkyl) acrylamides, and mixtures thereof. Most preferred is wherein X is a monomer unit selected from vinylpyridines.

E is a structural unit containing the ethylenically unsaturated moiety or "endcapping" group. Preferred is when E is selected from the group consisting of vinyl, allyl, acryloyl, methacryloyl, ethacryloyl, styryl, 3-vinylbenzyl, 4-vinylbenzyl, 3-vinylbenzoyl, 4-vinylbenzoyl, 1-butenyl, 1-propenyl, isobutenyl, isoprenyl, cyclohexyl, cylcopentyl, and mixtures thereof. More preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and mixtures thereof. Most preferred is when E is selected from the group consisting of vinyl, allyl, acryloyl, methacryloyl, ethacryloyl, 3-vinylbenzyl, 4-vinylbenzyl, and mixtures thereof.

I is an optionally present chemical moiety. In other words, n is an integer selected from zero and one. Without being limited by theory, I can be derived from a chemical initiator or solvent used in the synthesis of the B macromonomer. Nonlimiting examples of such initiators from which I can be derived include hydrogen ion, hydrogen radical, hydride ion, hydroxide ion, hydroxyl radical, peroxide radical, peroxide anion, C1–20 carbocations, C1–20 carbanions, C1–20 carbon radicals, C1–20 aliphatic and aromatic alkoxy anions, ammonium ion, and substituted ammonium ions (e.g., C1–20 alkyl and C1–20 alkoxy substituted). I can be derived from any useful solvent, nonlimiting examples of which inicude water, methanol ethanol, propanol, isopropanol, acetone, hexane, dichloromethane, chloroform, benzene, and toluene. Nonlimiting examples of I include chemical moieties selected from the group consisting of H, C1–C6 alkyl, phenyl, 4-methylphenyl, and benzyl; preferably H, methyl, ethyl, and phenyl; and more preferably H, methyl, and ethyl.

Representative examples of classes of endcapped B macromonomers useful herein include those selected from the group consisting of endcapped poly(N-alkyloxazolines), endcapped polyalkylene glycols, endcapped polyalkylene glycol monoalkyl ethers, endcapped poly(N-vinylpyrrolidones), endcapped poly(N-allylpyrrolidones), endcapped polyvinylpyridines, endcapped polyallylpyridines, endcapped polyvinylcaprolactams, endcapped polyallylcaprolactams, endcapped polyvinylimidazoles, endcappped polyallylimidazoles, endcapped polyvinylfurans, endcapped polyvinyltetrahydrofurans, endcapped polyallylfurans, endcapped polyacrylic acids, endcapped polymethacrylic acids, endcapped polyallyltetrahdyrofurans, endcapped polyvinylaminobenzenes, endcapped polyvinyl (N,N-dialkylaminobenzenes), endcapped polyvinyl (N-alkylaminobenznes), endcapped polyvinylaminomethylbenzenes, endcapped polyvinyl (N,N-dialkylaminomethylbenzenes), endcapped polyvinyl (N,alkylaminomethylbenzenes), endcapped polyvinylaminoethylbenzenes, endcapped polyvinyl (N,N-dialkylaminoethylbenzenes), endcapped polyvinyl (N-alkylaminoethylbenenes), endcapped poly(N,N-dialkylacrylamides), endcapped poly(N,N-dialkyl(alkyl) acrylamides), and mixtures thereof.

Preferred are macromonomers selected from the group consisting of endcapped poly(N-alkyloxazolines), endcapped polyalkylene glycols, endcapped polyalkylene glycol monoalkyl ethers, endcapped polyvinylpyridines, endcapped polyacrylamides, and mixtures thereof.

More preferred are endcapped polyvinylpyridine and endcapped polyacrylamide macromonomers.

Examples of endcapped poly(N-alkyloxazoline) macromonomers are those having the following chemical formula:

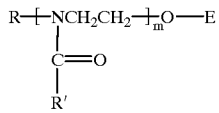

wherein R and R' are independently selected from H or $C_{1-8}$ straight or branched chain alkyl, more preferably R and R' are independently selected from H, methyl, or ethyl; and most preferably R is methyl and R' is ethyl. E is a copolymerizable, ethylenically unsaturated moiety (i.e. the endcapping moiety). Preferred is when E is selected from the group consisting of vinyl, allyl, acryloyl, methacryloyl, ethacryloyl, styryl, 3-vinylbenzyl, 4-vinylbenzyl, 3-vinylbenzoyl, 4-vinylbenzoyl, 1-butenyl, 1-propenyl, isobutenyl, isoprenyl, cyclohexyl, cylcopentyl, and mixtures thereof. More preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and mixtures thereof. Most preferred is when E is selected from the group consisting of vinyl, allyl, acryloyl, methacryloyl, ethacryloyl, styryl, 3-vinylbenzyl, 4-vinylbenzyl, and mixtures thereof. In the above structure m is preferably an integer from about 10 to about 2000, more preferably from about 15 to about 300, and most preferably from about 20 to about 250. Alternatively, other examples of endcapped poly (N-alkyloxazoline) macromonomers are those having the following chemical formula:

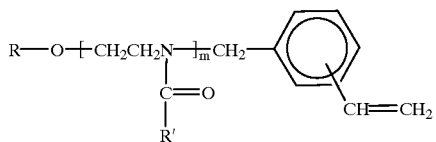

wherein R and R' are independently selected from the group consisting of H or $C_{1-8}$ straight or branched chain alkyl, more preferably R and R' are independently selected from H, methyl, or ethyl; and most preferably R is H and R' is ethyl. In the above structure m is an integer from about 10 to about 2000, more preferably from about 15 to about 300, and most preferably from about 20 to about 250. Highly preferred examples of endcapped poly(N-alkyloxazoline) macromonomers useful herein include acryloyl endcapped poly (2-ethyl oxazoline), methacryloyl endcapped poly(2-ethyl oxazoline), styryl endcapped poly(2-ethyloxazoline), acryloyl endcapped poly(2-methyl oxazoline), methacryloyl endcapped poly(2-methyl oxazoline), 3-vinylbenzoyl endcapped poly(2-methyloxazoline), 4-vinylbenzoyl endcapped poly(2-methyloxazoline), and mixtures thereof.

The endcapped poly(N-alkyloxazoline) macromonomers can be synthesized using standard synthetic procedures which involve polymerizing, usually under acid-catalyzed conditions, an N-alkyloxazoline to yield a poly(N- alkyloxazoline) alcohol. This alcohol can then be subsequently endcapped, employing standard reaction procedures, with the desired ethylenically unsaturated moiety using a reactive or activated form of an endcapping group. Suitable activated endcapping groups include vinyl, allyl, 1-propenyl, 3-vinylbenzyl, 4-vinylbenzyl, 3-vinylbenzoyl, and 4-vinylbenzoyl halides (e.g. chlorides, bromides, and iodides), and the acid chlorides and bromides derived from acrylic acid, methacrylic acid, and ethacrylic acid. See, e.g., S. I. Shoda et al., "Synthesis and Surfactant Property of Copolymers Having a Poly(2-Oxazoline) Graft Chain", *Journal of Polymer Science: Part A: Polymer Chemistry*, vol. 30, pp. 1489–1494 (1992); T. Saegusa et al., "Macromolecular Engineering on the Basis of the Polymerization of 2-Oxazolines, *Makromol. Chem., Macromol. Symp.*, vol. 51, pp. 1–10 (1991); S. Kobayashi et al., *Macromolecules*, vol 22, pp. 2878–2884 (1989), and U.S. Pat. No. 4,011,376, to Tomalia et al., issued Mar. 8, 1977; and U.S. Pat. No. 3,786,116, to Milkovich et al., issued Jan. 15, 1974; all of which are incorporated herein by reference.

Alternatively the polyoxazoline macromonomers can be synthesized by polymerizing the monomers onto an appropriate endcapping group. For example, the vinyl benzyl endcapped polyoxazolines can be prepared by polymerizing 2-ethyl-2-oxazoline onto a mixture of 3-vinylbenzyl and 4-benzylchlorides. See EXAMPLE III.

Also highly useful herein are endcapped polyalkylene glycol monoalkyl ether macromonomers corresponding to the following general chemical formula

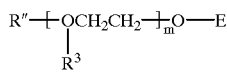

wherein R" is selected from C1–C40 straight or branched chain alkyl, more preferably from C1–C8 straight or branched chain alkyl, most preferably from C1–C4 straight or branched chain alkyl, and most preferably methyl; $R^3$ is selected from hydrogen, methyl, ethyl, or n-propyl, more preferably from hydrogen or methyl, most preferably from H. E is a copolymerizable, ethylenically unsaturated moiety (i.e. the endcapping moiety). Preferred is when E is selected from the group consisting of vinyl, allyl, acryloyl, methacryloyl, ethacryloyl, styryl, 3-vinylbenzyl, 4-vinylbenzyl, 3-vinylbenzoyl, 4-vinylbenzoyl, 1-butenyl, 1-propenyl, isobutenyl, isoprenyl, cyclohexyl, cylcopentyl, and mixtures thereof. More preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and mixtures thereof. Most preferred is when E is selected from the group consisting of vinyl, allyl, acryloyl, methacryloyl, ethacryloyl, styryl, 3-vinylbenzyl, 4-vinylbenzyl, and mixtures thereof. In the above structure, m is as described previously, wherein m is preferably an integer from about 20 to about 2000, more preferably from about 30 to about 750, and most preferably from about 40 to about 500. It is to be understood that in the above structure, that when $R^3$ is other than hydrogen that various isomers of the resulting macromonomer are possible depending upon the orientation of the individual glycol moieties. Therefore, the structure depicted above for these endcapped polyalkylene glycol monolkayl ethers is a general one that is not intended to limit these materials to any one particular isomeric structure.

Highly preferred examples of endcapped polyalkylene glycol monoalkyl ethers useful herein inlcude acryloyl endcapped polyethylene glycol monomethyl ether, 3-vinylbenzoyl endcapped polyethylene glycol monomethyl ether, 4-vinylbenzoyl endcapped polyethylene glycol monomethyl ether, methacryloyl endcapped polyethylene glycol monomethyl ether, and mixtures thereof.

The endcapped polyalkylene glycol monoalkyl ethers can be synthesized from the polyalkylene glycol monoalkyl ether and the reactive or activated form of an endcapping group employing standard reaction procedures. Suitable activated endcapping groups include vinyl, allyl, 3-vinylbenzoyl, and 4-vinylbenzoyl halides (e.g. chlorides, bromides, and iodides), and the acid chlorides and bromides derived from acrylic acid, methacrylic acid, and ethacrylic acid. The polyalkylene glycol monoalkyl ether can be synthesized from the corresponding polyalkylene glycol using any of the alkylating agents well known in the art (e.g., methyl iodide, methyl bromide, diazomethane, methyl sulfate, ethyl iodide). Polyethylene glycols of various molecular weight ranges, as well as their methyl ethers are commercially available from Aldrich Chemical Company and Union Carbide Corporation. Alternatively, the polyalkylene glycols can be synthesized from the corresponding alkylene oxides and alkylene glycols using standard synthetic procedures (e.g., the acid or base catalyzed polymerization of alkylene oxides).

Also highly useful herein are endcapped hydrophilic nitrogen-containing macromonomer units copolymerizable with A corresponding to the formula

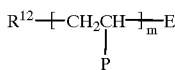

wherein E is a copolymerizble, ethylenically unsaturated moiety (i.e. the endcapping moiety). Preferred is when E is selected from the group consisting of vinyl, allyi, acryloyl, methacryloyl, ethacryloyl, 2-vinyl benzyl 3-vinyl benzyl, 4-vinyl benzyl, 2-vinylbenzoyl, 3-vinylbenzoyl, 4-vinylbenzoyl, 1-butenyl, isobutenyl, isoprenyl, cyclopentenyl, cyclohexenyl, and mixtures thereof. More preferred is when E is selected from the group consisting of vinyl, allyl, acryloyl, methacryloyl, ethacryloyl, 2-vinylbenzyl, 3-vinylbenzyl, 4-vinylbenzyl, 3-vinylbenzoyl, 4-vinylbenzoyl, and mixtures thereof. Most preferred is when E is selected from the group consisting of 2-vinylbenzyl, 3-vinylbenzoyl, 4-vinylbenzyl and mixtures thereof. $R^{12}$ is selected form the group consisting of hydrogen, C1–6 straight or branched chain alkyl, benzyl, 1-phenyl substituted C2–6 straight or branched chain alkyl, 1,1-diphenyl substituted C2–6 straight or branched chain alkyl, and mixtures thereof. More preferably $R^{12}$ is 1,1-diphenyl-4-methylpentyl. P is selected from the group consisting of 2-pyridyl, 3-pyridyl, 4-pyridyl, halogen substituted 2-, 3-, or 4-pyridyl, C1–4 alkyl substituted 2-, 3-, or 4-pyridyl, 2-aminophenyl, 3-aminophenyl, 4-aminophenyl, 2-aminomethylphenyl, 3-aminomethylphenyl, 4-aminomethylphenyl, and pharmaceutically acceptable salts and quaternized derivatives thereof, and mixtures thereof. In the preceding structure, m is preferably an integer from about 10 to about 2000, more preferably from about 15 to about 300, and most preferably from about 20 to about 250.

In the preceding structure it is found that pharmaceutically acceptable salts and quaternized derivatives are especially preferred because of their highly desired physical characteristics and solubility characteristics. By pharmaceutically acceptable salt as used herein is meant a salt that is generally regarded as safe for human use without undue risk of toxicity and other adverse effects. Nonlimiting examples of pharmaceutically acceptable salts of these materials include hydrochloride salts and hydrobromide salts. Nonlimiting examples of quaternized derivatives include alkyl quaternized derivatives wherein said alkyl group is a C1–30 straight or branched chain moiety, preferably a C1–4 straight or branched chain moiety, more preferably wherein said alkyl group is methyl or ethyl.

Highly preferred examples of these endcapped nitrogen containing macromonomers useful herein include acryloyl endcapped poly(2-, 3-, or 4-vinyl pyridine), acryloyl endcapped poly(2-, 3-, or 4-vinyl ethylsubstituted pyridine), methacryloyl endcapped poly(2-, 3-, or 4-vinyl pyridine), 2-, 3-, or 4-vinyl benzyl edncapped poly(2-, 3-, or 4-vinylpyridine), 2-, 3-, or 4-vinyl benzyl endcapped poly (2-, 3-, or 4-vinyl pyridine hydrochloride), 2-, 3-, or 4-vinyl benzyl endcapped poly(2-, 3-l or 4-vinyl methyl-quaternized pyridine), 2-, 3-, or 4-vinyl benzyl endcapped poly(4-dimethylaminomethylvinylbenzene), 2-, 3-, or 4- vinyl benzyl endcapped poly(alkyl-quaternized dimethylaminoethylvinylbenzene), and mixtures thereof.

These nitrogen containing endcapped macromonomers can be synthesized using standard synthetic procedures which involve polymerizing, usually under anionic initiation conditions the appropriate monomer unit, (e.g. 2-, 3-, or 4- vinyl pyridine, 4-dimethylaminomethyl vinyl benzene, etc.). A wide variety of initiators can be used, nonlimiting examples of which include bases such as n-butyl lithium, sec-butyl lithium, t-butyl lithium, lithium aluminum hydride, sodium hydride, and the like. Nonlimiting examples of these bases are provided in *Anionic Polymerization: Principles and Practice*, Maurice Morton, Chapter 2, p. 13, Academic Press, N.Y. (1983), which is incorporated by reference herein in its entirety. It has been found especially convenient to use these strong bases in conjunction with sterically hindered hydrocarbon materials such as 1,1-diphenyl ethylene to generate a sterically hindered base for inititiaing the polymerization reaction, in which case, the sterically hindered hydrocarbon is the actual initiator, defined previously as "I", which is incorporated into the macromonomer structure. Once the desired degree of polymerization is achieved, an appropriate endcapping reagent is typically used to terminate the polymerization and to endcap the macromonomer, nonlimiting examples of these endcapping reagents include 2-vinylbenzyl chloride, 3-vinylbenzyl chloride, 4-vinylbenzyl chloride, and the like.

The pharmaceutically acceptable salts and quaternized derivatives of these nitorgen containing macromonomers are readily prepared from the macromonomers using standard synthetic procedures. Typically, the macromonomers are reacted with an acid to form the salt. For example reaction with hydrochloric acid or hydrobromic acid (either gaseous or as an aqueous solution) would yield the corresponding hydrochloride and hydrobromide salts, respectively. To form the quaternized derivatives the macromoners are reacted with a quaternizing agent. For example reaction with a methyl halide (e.g., methyl iodide, methyl chloride) or an alkyl sulfate (e.g. dimethyl sulfate, diethylsulfate) would yield the corresponding quaternized macromonomer.

More typically, the pharmaceutically acceptable salt or quaternized derivative of the thermoplastic elastomeric polymer is desired, in which case the non-salt form or non-quaternized macromonomer is incorporated into the thermoplastic elastomeric copolymer, followed by salt formation or quaternization of the copolymer using standard synthetic procedures analogous to those described for the macromonomer.

Also highly useful herein are endcapped hydrophilic polyacrylamide macromonomer units copolymerizable with A corresponding to the formula

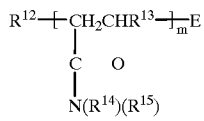

wherein E is a copolymerizable, ethylenically unsaturated moiety (i.e. the endcapping moiety). Preferred is when E is selected from the group consisting of vinyl, allyl, acryloyl, methacryloyl, ethacryloyl, 2-vinyl benzyl, 3-vinyl benzyl, 4-vinyl benzyl, 2-vinylbenzoyl, 3-vinylbenzoyl, 4-vinylbenzoyl, 1-butentyl, isobutenyl, isoprenyl, cyclohexyl, cyclopententyl, cyclohexenyl, and mixtures thereof. More preferred is when E is selected from the group consisting of vinyl, allyl, acryloyl, methacryloyl, ethacryloyl, 2-vinylbenzyl, 3-vinylbenzyl, 4-vinylbenzyl, 3-vinylbenzoyl, 4-vinylbenzoyl, and mixtures thereof. Most preferred is when E is selected from the group consisting of 2-vinylbenzyl, 3-vinylbenzyl, 4-vinylbenzyl and mixtures thereof. $R^{12}$ is selected from the group consisting of hydrogen, $C_1$–$C_6$ straight or branched chain alkyl, benzyl, 1-phenyl substituted $C_{2\text{-}6}$ straight or branched chain alkyl, 1,1-diphenyl substituted $C_{2\text{-}6}$ straight or branched chain alkyl, and mixtures thereof.

$R^{13}$ is selected from the group consisting of H and $C_{1\text{-}6}$ straight or branched chain alkyl, more preferably H and $C_1$–C4 straight or branched chain alkyl, and most preferably H, methyl, and ethyl. $R^{14}$, and $R^{15}$ are independently selected from the group consisting of C1–8 straight or branched chain alkyl; more preferably C1–6 straight or branched chain alkyl, and most preferably methyl. In the preceding structure, m is preferably an integer from about 10 to about 2000, more preferably from about 15 to about 3000, and most preferably from about 20 to about 250.

Polymers of the Present Invention

Particularly preferred polymers for use in the present invention include the following (the weight percents below refer to the amount of reactants added in the polymerization reaction, not necessarily the amount in the finished polymer):

N-butyl acrylate/2-methoxyethyl acrylate/Poly(4-dimethylmino methylvinyl benzene) 38/22/40

Methyl quaternized N-butyl acrylate/2-methoxyethyl acrylate/poly(4-dimethylaminomethylvinyl benzene) 38/22/40

Ethyl quaternized N-butyl acrylate/2-methoxyethyl acrylatelpoly(2-vinylpyridine) 38/22/40

N-butyl acrylate/2-methoxyethyl acrylate/Poly(2-vinylpyridine) hydrochloride 38/22/40 n-butyl acrylate/2-methoxyethyl acrylate/poly(N,N-dimethylacrylamide) 38/22/40 n-butyl acrylate/2-methoxyethyl acrylate/poly(N,N-dimethylmethacrylamide) 38/22/40 n-butyl acrylate/2-methoxyethyl acrylate/poly(2-ethyl-2-oxazoline) 38/22/40 n-butyl acrylate/2-methoxyethyl acrylate/poly(2-ethyl-2-oxazoline) 38/22/40 n-butyl acrylate/2-methoxyethyl acrylate/poly(2-ethyl-2-oxazoline) 35/25/40 n-butyl acrylate/2-methoxyethyl acrylate/poly(2-ethyl-2-oxazoline) 38/22/40 n-butyl acrylate/2-methoxyethyl acrylate/poly(2-ethyl-2-oxazoline) 38/22/40 n-butyl acrylate/poly(2-ethyl-2-oxazoline) 60/40 n-butyl acrylate/2-ethylhexyl methacrylate/poly(2-ethyl-2-oxazoline) 40/20/40 n-butyl acrylate/2-methoxyethyl acrylate/poly(ethylene glycol) 386/22140 n-butyl acrylate/2-(dimethylamino)ethyl methacrylate/poly(2-ethyl-2-oxazoline) 36/24/40 n-butyl acrylate/methyl quaternized 2-(dimethylamino) ethyl methacrylate/poly(2-ethyl-2-oxazoline) 36/24/40

Synthesis of the Copolymers

In general, the copolymers can be made by free radical polymerization of the A monomers with the B macromonomers. It is not intended to necessarily exclude from this invention any copolymers made by means other than free radical polymerization, so long as the product has the desired physical properties. The copolymers herein contain randomly repeating monomer units and macromonomer units.

The general principles of free radical polymerization methods are well understood. See, for example, Odian, "Principles of Polymerization", 2nd edition, John Wiley & Sons, 1981, pp. 179–318. The desired monomers and macromonomers are all placed in a reactor, along with a sufficient amount of a mutual solvent so that when the reaction is complete the viscosity of the reaction is reasonable. Typical monomer and macromonomer loadings are from about 10% to about 50%, on a weight basis. Undesired terminators, especially oxygen, can be removed as needed. This is done by evacuation or by purging with an inert gas, such as argon or nitrogen. The initiator is introduced and the reaction brought to the temperature needed for initiation to occur, assuming thermal initiators are used. Nonlimiting examples of suitable initiators include those selected from the group consisting of azo initiators, peroxide initiators, redox initiators, and photochemical initiators. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as needed utilizing a variety of techniques including filtration, extraction, trituration, membrane separation, gel permeation chromatography, and like.

There are numerous variations on these procedures which are entirely up to the discretion of the synthetic chemist (e.g., choice of degassing method and gas, choice of initiator type, extent of conversion, reaction loading, etc). The choice of initiator and solvent are often determined by the requirements of the particular monomers and macromonomer used, because different monomers and macromonomers have different solubilities and different reactivities to a specific initiator.

The copolymers of the present invention can also be synthesized by first presparing the backbone from the polymerization of suitable monomers, followed by further polymerization of the backbone with suitable hydrophilic monomers to form the polymeric side chains. This alternative procedure for synthesizing the copolymers herein is illustrated in EXAMPLE VII below.

When salts and/or quaternized polymers are desired, these polymers are readily prepared from the copolymers using standard procedures, such as reaction with a strong acid or a quaternizing agent. Preferred among the acids are hydrogen chloride and hydrogen bromide, which can be employed either as a gas or as an aqueous solution. Commonly used quaternizing agents include alkyl halides (e.g., methyl iodide and methyl chloride) and alkyl and dilakyl suflates (e.g., dimethyl sulfate and diethyl sulfate).

Analysis of the copolymer reaction product and the extracted materials, and the purified copolymer can be perfomred by conventional analysis techniques known in the art. These include, for example, nuclear magnetic resource (NMR), infrared molecular spectroscopies, gel permeation/size exclusion chromatography, membrane osmometry, and atomic absorption and emission spectroscopies.

Hair Care and Topical Skin Care Compositions

The copolymers of the present invention can be formulated into a wide variety of product types, including mousses, gels, lotions, tonics, sprays, shampoos, conditioners, rinses, hand and body lotions, facial moisturizers, sunscreens, anti-acne preparations, topical analgesics, mascaras, and the like. The carriers and additional components required to formulate such products vary with product type and can be routinely chosen by one skilled in the art. The following is a description of some of these carriers and additional components.

Carriers

Hair Care Compositions

The hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular copolymer to be used, and whether the product formulated is meant to be left on the surface to which it is applied (e.g., hair spray, mousse, tonic, or gel) or rinsed off after use (e.g., shampoo, conditioner, rinse).

The carriers used herein can include a wide range of components conventionally used in hair care compositions. The carriers can contain a solvent to dissolve or disperse the particular copolymer being used, with water, the C1–C6 alcohols, and mixtures thereof being preferred; and water, methanol, ethanol, isopropanol, and mixtures thereof being more preferred. The carriers can also contain a wide variety of additional materials inlcuding, but not limited to acetone, hydrocarbons (such as isobutane, hexane, decene), halogenated hydrocarbons (such as Freons), linalool, esters (such as ethyl acetate, dibutyl phthalate), and volatile silicon derivatives (especially siloxanes such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane, cyclomethicone, and dimethicone having for example, a viscosity at 25° C. of about 15 centipoise or less), and mixtures thereof. When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilize any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilize an emulsifying agent. Examples of suitable emulsifying agents include nonionic, cationic, anionic surfactants, or mixtures thereof. Fluorosurfactants are especially preferred, particularly if the product is a hair spray composition and most especially if it is a spray composition having relatively low levels of volatile organic solvents, such as alcohols, and relatively high levels of water (e.g., in excess of about 10%, by weight water). If such an emulsifying agent is used, it is preferably present at a level of from about 0.01% to about 7.5% of the composition. The level of propellant can be adjusted as desired but is generally from about 3% to about 30% of mousse compositions and from about 15% to about 50% of the aerosol hair spray compositions.

Suitable spray containers are well known in the art and include conventional, non-aerosol pump sprays i.e., "atomizers," aerosol containers or cans having propellant, as described above, and also pump aerosol containers utilizing compressed air as the propellent. Pump aerosol containers are disclosed, for example, in U.S. Pat. Nos. 4,077,441, Mar. 7, 1978, Olofsson and 4,850,577, Jul. 25, 1989, TerStege, both incorporated by reference herein, and also in U.S. Ser. No. 071839,648, Gosselin, Lund, Sojka, and Lefebvre, filed Feb. 21, 1992, "Consumer Product Package Incorporating A Spray Device Utilizing Large Diameter Bubbles. Pump aerosols hair sprays using compressed air are also currently marketed by The Procter & Gamble Company under their tradename VIDAL SASSOON AIRSPRAYR hair sprays.

Where the hair care compositions are conditioners and rinses the carrier can include a wide variety of conditioning materials. Where the hair care compositions are shampoos, the carrier can include surfactants, suspending agents, thickeners etc. Various additional components useful in hair care compositions are described in U.S. Pat. No. 5,106,609, to Bolich, Jr. et al., issued Apr. 21, 1992; and U.S. Pat. No. 4,387,090, to Bolich, Jr. issued Jun. 7, 1983; which are incorporated by reference herein. Some of these additional components are described below.

Topical Skin Care Compositions

The topical cosmetic and pharmaceutical compositions of the present invention can comprise a carrier. The carrier should be "cosmetically and/or pharmaceutically acceptable", which means that the carrier is suitable for topical application to the skin, has good aesthetic properties, is compatible with the copolymers of the present invention and any other components, and will not cause any untoward safety or toxicity concerns.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" Cosmetics & Toiletries, vol. 105, pp. 122–139 (December 1990); "Sun Products Formulary", Cosmetics & Toiletries, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers of the skin care compositions can comprise from about 50% to about 99% by weight of the compositions of the present invention, preferably from about 75% to about 99%, and most preferably from about 85% to about 95%.

Preferred cosmetically and/or pharmaceutically acceptable topical carriers include hydro-alcoholic systems and oil-in-water emulsions. When the carrier is a hydro-alcoholic system, the carrier can comprise from about 1% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. Additional components useful in formulating these topical compositions are further described below.

Additional Components

A wide variety of additional components can be employed in the hair care and topical skin compositions herein. Non-limiting examples include the following:

Pharmaceutical Actives

The compositions of the present invention, especially the topical skin care compositions, can comprise a safe and effective amount of a pharmaceutical active. The phrase "safe and effective amount", as used herein, means an amount of an active high enough to significantly or positively modify the condition to be treated, but low enough to avoid serious side effects (at a reasonable benefit/risk ratio), within the scope of sound medical judgement. A safe and effective amount of the pharmaceutical active will vary with the specific active, the ability of the composition to penetrate the active through the skin, the amount of composition to be applied, the particular condition being treated, the age and physical condition of the patient being treated, the severity of the condition, the duration of the treatment, the nature of concurrent therapy, and like factors.

The pharmaceutical actives which can be used in the compositions of the present invention preferably comprise from about 0.1% to about 20% by weight of the compositions, more preferably from about 0.1% to about 10%, and most preferably from about 0.1% to about 5%. Mixtures of pharmaceutical actives may also be used.

Nonlimiting examples of pharmaceutical actives can include the following:

Useful pharmaceutical actives in the compositions of the present invention include anti-acne drugs. Anti-acne drugs preferred for use in the present invention include the keratolytics such as salicylic acid, sulfur, lactic acid, glycolic, pyruvic acid, urea, resorcinol, and N-acetylcysteine; retinoids such as retinoic acid and its derivatives (e.g., cis and trans); antibiotics and antimicrobials such as benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate, and cholate. Preferred for use herein is salicylic acid.

Useful pharmacetuical actives in the compositions of the present invention include non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Useful pharmaceutical actives in the compositions of the present invention include antipruritic drugs. Antipruritic drugs preferred for inclusion in compositions of the present invention include pharmaceutically-acceptable salts of methdilizine and trimeprazine. Useful pharmaceutical actives in the compositions of the present invention include include anesthetic drugs. Anesthetic drugs preferred for inclusion in compositions of the present invention include pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine and phenol. Useful pharmaceutical actives in the compositions of the present invention include antimicrobial drugs (antibacterial, antifungal, antiprotozoal and antiviral drugs). Antimicrobial drugs preferred for inclusion in compositions of the present invention include pharmaceutically-acceptable salts of b-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole.

Also useful herein are sunscreening agents. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Preferred among those sunscreens which are useful in the compositions of the instant invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyidibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2ethylhexyl) methylaminobenzoic acid ester of 2-hydroxy4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Also useful in the present invention are sunless tanning agents including dihydroxyacetone, glyceraldehyde, indoles and their derivatives, and the like. These sunless tanning agents may also be used in combination with the sunscreen agents.

Other useful actives include skin bleaching (or lightening) agents including but not limited to hydroquinone, ascorbic acid, kojic acid and sodium metabisulfite.

Other useful actives which are especially useful for hair care compositions include anti-dandruff actives such as zinc pyrithione, octopirox, selenium disulfide, sulfur, coal tar, and the like.

Conditioners

Conditioning agents useful herein, and especially useful for hair care compositions, include hydrocarbons, silicone fluids, and cationic materials.

The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Silicone conditioning agents useful herein can include either cyclic or linear polydimethylsiloxanes, pheny and alkyl phenyl silicones, and silicone copolyols. The linear volatile silicones generally have viscosities of less than about 5 centistokes at 25° C., while the cylic materials have viscosities less than about 10 centistokes.

Cationic conditioning agents useful herein can include quaternary ammonium salts or the salts of fatty amines. Preferred quaternary ammonium salts are dialkyl dimethyl ammonium chlorides, wherein the alkyl groups have from 12 to 22 carbon atoms and are derived from long-chain fatty acids. Representative examples of quaternary ammonium salts include ditallow dimethyl ammonium chloride, ditallow dimethyl ammonium methyl sulfate, dihexadecyl dimethyl ammonium chloride, and di(hydrogenated tallow) ammonium chloride. Other qauternary ammonium salts useful herein are dicationics such as tallow propane diammonium dichloride. Quaternary imidazolinium salts are also useful herein. Examples of such materials are those imidazolinium salts containing C12–22 alkyl groups such as 1-methyl-1-[(stearoylamide)ethyl]-2-heptadecyl-4, 5-dihydroimidazolinium chloride, 1-methyl-1-[(palmitoylamide)ethyl]-2-octadecyl-4,5-dihydroimidazolinium chloride and 1-methyl-1-[(tallowamide)-ethyl]-2-tallow-imidazolinium methyl sulfate. Also useful herein are salts of fatty amines. Examples of such compounds include stearylamine hydrochloride, soyamine hydrochloride, and stearylamine formate. Useful conditioning agents are disclosed in U.S. Pat. No. 4,387,090, to Bolich, issued Jun. 7, 1983, which is incorporated by reference herein.

Humectants and Moisturizers

The compositions of the present invention can contain one or more humectant or moisturizing materials. A variety of these materials can be employed and each can be present at a level of from about 0.1% to about 20%, more preferably from about 1% to about 10% and most preferably from about 2% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Preferred humectants and moisturizers are glycerol, butylene glycol, hexylene glycol, and mixtures thereof.

Surfactants

The compositions of the present invention, especially the shampoo and conditioner compositions, can contain one or more surfactants. These surfactants are useful adjuncts for the carriers of the present compositions, and are not required for solubilizing or dispersing the copolymers of the present invention. For a shampoo, the level is preferably from about 10% to about 30%, preferably from 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants. A wide variety of surfactants useful herein are disclosed in U.S. Pat. No. 5,151,209, to Mc Call et al., issued Sep. 29, 1992; U.S. Pat. No. 5,151,210, to Steuri et al., issued Sep. 29, 1992; and U.S. Pat. No. 5,120,532, to Wells et al., issued Jun. 9, 1992, all of which are incorporated by reference herein.

Nonlimiting examples of these surfactants include anionic surfactants such as alkyl and alkyl ether sulfates. These materials typically have the respective formulae $ROSO_3M$ and $RO(C_2H_4O)_xSO_3M$, wherein R is alkyl or alkenyl of from about 10 to about 20 carbon atoms, x is 1 to 10, and M is a water-soluble cation such as ammonium, sodium, potassium and triethanolamine. Another suitable class of anionic surfactants are the water-soluble salts of the organic, sulfuric acid reaction products of the general formula:

$$R_1\text{—}SO_3\text{—}M$$

wherein $R_1$ is chosen from the group consisting of a straight or branched chain, saturated aliphatic hydrocarbon radical having from about 8 to about 24, preferably about 12 to about 18, carbon atoms; and M is a cation. Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Still other anionic synthetic surfactants include the class designated as succinamates, olefin sulfonates having about 12 to about 24 carbon atoms, and b-alkyloxy alkane sulfonates. Many additional nonsoap synthetic anionic surfactants are described in *McCutcheon's, Detergents and Emulsifiers*, 1984 *Annual*, published by Allured Publishing Corporation, which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants useful herein are preferably used in combination with an anionic, amphoteric or zwitterionic surfactant. These nonionic surfactants can be broadly defined as compounds produced by the condensation of alkylene oxide groups (hydrophilic in nature) with an organic hydrophobic compound, which may be aliphatic or alkyl aromatic in nature.

Cationic surfactants useful in compositions of the present invention are disclosed in the following documents, all incorporated by reference herein: M.C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. Other zwitterionics such as betaines are also useful in the present invention. Examples of betaines include the high alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma carboxypropyl betaine, lauryl bis-(2-hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine).

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Carboxylic Acid Copolymer Thickeners

Another component useful in the compositions herein is a carboxylic copolymer thickener. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred polymers for use herein are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e. a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, *CTFA International Cosmetic Ingredient Dictionary*, fourth edition, 1991, pp. 12 and 80; which are also incorporated herein by reference.

Examples of commercially availble hompolymers of the first type useful herein include the carbomers, which are homopolymers of acrylic acid crosslinked with allyl ethers of sucrose or pentaerytritol. The carbomers are available as the Carbopol® 900 series from B. F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commerically available as Carbopole® 1342, Pemulen TR-1, and Pemulen TR-2, from B. F. Goodrich. In other words, examples of carboxylic acid polymer thickeners useful herein are those selected from the group consisting of carbomers, acrylates/C10–C30 alkyl acrylate crosspolymers, and mixtures thereof.

The compositions of the present can comprise from about 0.025% to about 1%, more preferably from about 0.05% to about 0.75% and most preferably from about 0.10% to about 0.50% of the carboxylic acid polymer thickeners.

Emulsifiers

The compositions herein can contain various emulsifiers. These emulsifiers are useful for emulsifying the various carrier components of the compositions herein, and are not required for solubilizing or dispersing the copolymers of the present invention. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5% of the compositions of the present invention.

Emollients

The compositions useful in the methods of the present invention can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 1% to about 50%, preferably from about 1% to about 25%, and more preferably from about 1% to about 10% by weight of the compositions useful in the present invention.

Additional Components

A variety of additional components can be incorporated into the compositions herein. Non-limiting examples of these additional components include vitamins and derivatives thereof (e.g., ascorbic acid, vitamin E, tocopheryl acetate, retinoic acid, retinol, retinoids, and the like); low pH thickening agents (e.g. polyacrylamide and $C_{13-14}$ isoparaffin and laureth-7, available as Sepigel from Seppic Corporation; polyquaternium and mineral oil, available as Salcare SC92, from Allied Colloids; crosslinked methyl quaternized dimethylaminomethacrylate and mineral oil, available as Salcare SC95 from Allied Colloids; resins; gums and thickeners such as xanthan gum, carboxymethyl cellulose, hydroxymethyl cellulose, hydroxyethyl cellulose, alkyl-modified hydroxyalkyl celluloses (e.g. long chain alkyl modified hydroxyethyl celluloses such as cetyl hydroxyethylcellulose), and magnesium aluminum silicate; cationic polymers and thickeners (e.g., cationic guar gum derivatives such as guar hydroxypropyltrimonium chloride and hydroxypropyl guar hydroxypropyltrimonium chloride, available as the Jaguar C series from Rhone-Poulenc; polymers for aiding the film-forming properties and substantivity of the composition (such as a copolymer of eicosene and vinyl pyrrolidone, an example of which is available from GAF Chemical Corporation as Ganex® V-220); suspending agents such as ethylene glycol distearate and the like; preservatives for maintaining the antimicrobial integrity of the compositions; skin penetration aids such as DMSO, 1-dodecylazacycloheptan-2-one (available as Azone from the Upjohn Co.) and the like; antioxidants; chelators and sequestrants; and aesthetic components such as fragrances, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like.

Method of Using Hair and Skin Care Compositions

The hair care and skin care compositions of the present invention are used in conventional ways to provide the desired benefit appropriate to the product such as hair styling, holding, cleansing, conditioning and the like for hair care compositions and benefits such as moisturization, sun protection, anti-acne, anti-wrinkling, artificial tanning, analgesic, and other cosmetic and pharmaceutical benefits for skin care compositions. Such methods of use depend upon the type of composition employed but generally involve application of an effective amount of the product to the hair or skin, which may then be rinsed from the hair or skin (as in the case of shampoos and some conditioning products) or allowed to remain on the hair (as in the case of spray, mousse, or gel products), or allowed to remain on the skin (as in the case of the skin care compositions). By "effective amount" is meant an amount sufficient to provide the benefit desired. Preferably, hair rinse, mousse, and gel products are applied to wet or damp hair prior to drying and styling of the hair. After such compositions are applied to the hair, the hair is dried and styled in the usual ways of the user. Hair sprays are typically applied to dry hair after it has already been dried and styled. Cosmetic and pharmaceutical topical skin care compositions are applied to and rubbed into the skin.

The following examples further illustrate preferred embodiments within the scope of the present invention. The examples are given solely for the purposes of illustration and are not to be construed as limitations of the present invention as many variations of the invention are possible without departing from its spirit and scope.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example I

Synthesis of Poly(2-ethyl-2-oxazoline) Alcohol

To a solution of 50 g (0.5044 mol) of 2-ethyl-2-oxazoline in 50 mL of acetonitrile is added 0.92 g (0.0048 mol) of methyl-p-toluenesulfonate at 0° C. under a nitrogen atmosphere. The reaction mixture is heated at 80° C. for 20 hours and the resulting polymer solution is then refluxed with 2.3 mL distilled water in the presence of 5.6 g (0.0528 mol) of sodium carbonate for 24 hours. The solvents are removed under vacuum. The residue is extracted with 300 mL of dichloromethane for 24 hours, and the insolubles are removed by suction filtration. The dichloromethane is then evaporated to yield about 48 g (96% yield) of poly(2ethyl-2-oxazoline) alcohol.

Example II

Synthesis of Acrylate-Capped Poly(2-ethyl-2-oxazoline) Alcohol Macromonomer

To a solution of 48 g of poly(2-ethyl-2-oxazoline) alcohol (from EXAMPLE I) and 1.0 g (0.01056 mol) of triethylamine in 80 mL of dichloromethane is added dropwise a solution of 0.95 g (0.01056 mol) of acryloyl chloride at 0° C. under a nitrogen atmosphere. The reaction mixture is then stirred at room temperature for 36 hrs, and the resulting solution is then suction filtered to remove the insolubles. The solvent and any unreacted triethylamine are removed by evaporation under vacuum. The resulting solid is then redissolved in 200 mL of dichloromethane, filtered, and evaporated under vacuum to yield about 45.6 g (95% yield) of the macromonomer.

Using an analogous procedure the methacrylate and ethacrylate endcapped macromonomers are prepared by replacing the acryloyl chloride with an equivalent molar amount of methacryloyl chloride and ethacryloyl chloride, respectively.

Example III
Synthesis of Vinvibenzyl-Capped Poly(2-ethyl-2-oxazoline) Alcohol Macromonomer To a solution of 50 g (0.5044 mol) of 2-ethyl-2-oxazoline in 50 mL of acetonitrile is added a mixture of 0.3816 g (0.0025 mol) of meta and paravinylbenzylchlorides (available from Aldrich Chemical Co.), 0.562 g (0.0037 mol) of sodium iodide and 0.06 g (0.00023 mol) of N,N'-diphenyl-p-phenylenediamine. The solution is then heated at 90° C. for 16 hours. To the resulting reaction product is added 100 mL of dichloromethane and the solution is filtered and then precipitated in 800 mL of ether. The precipitate product is collected by vacuum filtration and dried under vacuum at ambient temperature to yield about 45 g (90% yield) of the macromonomer.

Example IV
Synthesis of Acrylate-Capped Poly(ethylene glycol)methyl Ether Macromonomer To a solution of 50 g (0.01 mol) of poly(ethylene glycol) methyl ether having an average molecular weight of about 5000 (commercially available from Aldrich Chemical Co.) and 4.05 g (0.04 mol) of triethylamine in 400 mL of dichloromethane is added dropwise at 0° C. under a nitrogen atmosphere a solution of 2.26 g (0.025 mol) of acryloyl chloride dissolved in 25 mL of dichloromethane. The reaction mixture is then stirred at room temperature for 36 hrs, and the resulting solution is then suction filtered to remove the insolubles. The solvent and any unreacted triethylamine are removed by evaporation under vacuum. The resulting solid is then redissolved in 300 mL of dichloromethane, filtered, and evaporated under vacuum to yield about 50 g (100% yield) of the macromonomer.

The above procedure is varied using other poly(ethylene glycol)alkyl ethers (e.g. methyl, ethyl, 2-ethylhexyl, decyl, dodecyl, cetyl, stearyl, lauryl, and myristyl wherein the polymer has an average molecular weight varying from about 1000 to about 200,000) to obtain the analogous acrylate-capped macromonomers. Additionally, the methacrylate and ethacrylate endcapped macromonomers are prepared by replacing the acryloyl chloride with an equivalent molar amount of methacryloyl chloride and ethacryloyl chloride, respectively.

Example V
Synthesis of Poly(n-butyl acrylate)-graft-poly(2-ethyl-2-oxazoline) Thermoplastic Elastomeric Copolymer To a solution of 16.0 g (0.1248 mol) of n-butyl acrylate, and 4 g of acrylate capped poly(2-ethyl-2-oxazoline) macromonomer (from Example II) in 100 mL of acetone is added 0.03 g (0.00018 mol) of azoisobutyronitrile (AIBN) initiator. The resulting solution is refluxed slowly for about 20 hours. The reaction is then quenched by the addition of about 5 mL of methanol. The solution is then poured into a teflon pan and the acetone is evaporated at room temperature under a fume hood. The resulting polymer film is redissovied in ethanol, filtered, and the ethanol is then evaporated to yield about 18.4 g of the thermoplastic elastomeric copolymer.

Alternatively, by varying the monomers and macromonomers used, this procedure is used to prepare other copolymers of the present invention.

EXAMPLE VI
Synthesis of Poly(n-butyl-co-2-methoxvethylacrylate)-graft-poly(2-ethyl-2-oxazoline) Thermoplastic Elastomeric Copolymer: Method I To a solution of 4.5 g (0.035 mol) of n-butyl acrylate, 2.5 g (0.0192 mol) of 2-methoxy ethylacrylate and 3 g poly(2-ethyl-2-oxazoline) macromonomer (from Example II) in 40 mL of acetone is added 0.05 g of AIBN initator. The resulting solution is refluxed slowly for about 20 hours. The reaction is then quenched by the addition of about 5 mL of methanol. The solution is then poured into a teflon pan and the acetone is evaporated at room temperature under a fume hood. The resulting polymer film is redissovled in ethanol, filtered, and the ethanol is then evaporated to yield about 9.5 g of the thermoplastic elastomeric copolymer.

Alternatively, by varying the monomers and macromonomers used, this procedure is used to prepare other copolymers of the present invention.

Example VII
Synthesis of Poly(n-butyl-co-2-methoxyethvlacrylate)-graft-poly(2-ethyl-2-oxazoline) Thermoplastic Elastomeric Corolymer: Method II To a 500 mL round-bottomed flask is added 20.8 g (0.1623 mol) of n-butyl acrylate, 11.2 g (0.0861 mol) of 2-methoxyethyl acrylate, 0.30 g (0.002 mol) 2-vinylbenzyl chloride, and 0.02 g (0.0012 mol) of azoisobutyronitrile (AIBN) initator, in 200 mL of acetone. The resulting solution is refluxed slowly for about 24 hours. The reaction is then quenched by the addition of about 5 mL of methanol and cooled to room temperature. The solvents are removed by rotary evaporation and the resulting polymer is dissolved in 250 mL of dry acetonitrile. Next 20.0 g (0.2018 mol) of 2-ethyl-2-oxazoline and 0.44 g (0.0029 mol) of sodium iodide is added and the solution is heated to 90° C. for 20 hours. The resulting solution is filtered and the solvent is evaporated to yield about 45.0 g (86% yield) of the thermoplastic elastomeric copolymer.

Alternatively, by varying the monomers used, this procedure is used to prepare other copolymers of the present invention.

Example VIII
Synthesis of Poly(n-butyl-co-2-(dimethylamino)ethyl methacrylate)-graft-poly(2-ethyl-2-oxazoline) Thermoplastic Elastomeric To a solution of 7.2 g (0.0561 mol) of n-butyl acrylate, 4.8 g (0.0305 mol) of 2-(dimethylamino)ethyl methacrylate, and 8.0 g poly(2-ethyl-2-oxazoline) macromonomer (from Example II) in 80 mL of acetone is added 0.01 g of AIBN initator. The resulting solution is refluxed slowly for about 24 hours. The reaction is then quenched by the addition of about 5 mL of methanol. The solution is then poured into a teflon pan and the acetone is evaporated at room temperature under a fume hood. The resulting polymer film is redissovled in ethanol, filtered, and the ethanol is then is evaporated to yield about 18.4 g of the thermoplastic elastomeric copolymer.

Alternatively, by varying the monomers and macromonomers used, this procedure is used to prepare other copolymers of the present invention.

Example IX
Synthesis of Methyl Quaternized Poly(n-butyl-co-2-(dimethylamino)-ethyl methacrylate)graft-poly(2-ethyl-2-oxazoline) Thermoplastic Elastomeric Copolymer To 10 grams of the copolymer from EXAMPLE VIII dissovled in 80 grams of ethanol is added dropwise 4.32 g (0.0281 mole) of dimethylsulfate. The resulting solution is stirred for 2 hours at room temperature. The solvent is removed by rotary evorpation to yield about 10 grams of the methyl quaternized copolymer.

Example X
Hair Spray

Hair spray compositions are prepared from the following components utilizing conventional mixing techniques.

| | Weight % | | | |
|---|---|---|---|---|
| Ingredients | A | B | C | D |
| Water | QS 100 | QS 100 | QS 100 | QS 100 |
| Ethanol (SCA 40) | 79.0 | 79.0 | 79.0 | 90.0 |
| Copolymer of Example VI[1] | 4.0 | 4.0 | 3.0 | 3.0 |
| Fragrance | 0.1 | 0.2 | — | — |

[1]Alternatively, spray compositions are prepared using the copolymers of Examples V, VIII, XXII, XXIII, XXIV, and XXVI.

These products are prepared by first dissolving the polymer in the ethanol with stirring. The water and fragrance are then added with stirring. The resulting hair spray compositions can then be packaged in a nonaerosol spray pump. Alternatively, the compositions can be combined with conventional propellants and packaged in an aerosol spray.

These hair sprays are useful for application to the hair to provide a styling and holding benefit.

Example XI
Reduced Volatile Organic Content Hairspray

Hair spray compositions are prepared from the following components utilizing conventional mixing techniques.

| | Weight % | | | |
|---|---|---|---|---|
| Ingredients | A | B | C | D |
| Water | QS 100 | QS 100 | QS 100 | QS 100 |
| Ethanol | 54.0 | 54.0 | 54.0 | 54.0 |
| Copolymer of Example VI[1] | 4.0 | 3.0 | 4.0 | 3.0 |
| Fragrance | 0.05 | 0.2 | — | — |

[1]Alternatively, spray compositions are prepared using the copolymers of Examples V, VIII, XXII, XXIII, XXIV, and XXVI.

These products are prepared by first dissolving the polymer in the ethanol with stirring. The water and fragrance are then added with stirring. The resulting hair spray compositions can then be packaged in a nonaerosol spray pump. Alternatively, the compositions can be combined with conventional propellants and packaged in an aerosol spray.

These hair sprays are useful for application to the hair to provide a styling and holding benefit.

Example XII
Mousse

Mousse compositions are prepared from the following components utilizing conventional mixing techniques.

| | Weight % | | |
|---|---|---|---|
| Ingredients | A | B | C |
| Water | QS 100 | QS 100 | QS 100 |
| Copolymer of Example VIII[1] | 3.00 | 2.50 | 3.50 |
| Lauramide DEA | 0.33 | 0.33 | 0.33 |
| Sodium Methyl Oleyl Taurate | 1.67 | 1.67 | 1.67 |
| DMDM Hydantoin | 0.78 | 0.78 | 0.78 |
| Disodium EDTA | 0.20 | 0.20 | 0.20 |
| Polyoxyalkylated isostearyl alcohol[2] | 0.10 | 0.10 | 0.10 |
| Fragrance | 0.10 | 0.10 | 0.10 |
| Propellant[3] | 7.0 | 7.0 | 7.0 |

[1]Alternatively, mousse compositions are prepared using the copolymers of Examples V, VI, XXII, XXIII, XXIV, and XXVI.
[2]Available as Aerosurf 66-E10.
[3]Available as a mixture of 82.46% isobutane, 16.57% propane, and 0.001% butane.

These products are prepared by first dissolving the polymer in water with stirring. The remaining ingredients, except the propellant, are then added with stirring.

The resulting mousse concentrate can then be combined with conventional propellants (e.g., Propellant A46) and packaged in an aerosol spray.

These mousses are useful for application to the hair to provide a styling and holding benefit.

Example XIII
Hair Tonic

Hair tonic compositions are prepared from the following components utilizing conventional mixing techniques.

| | Weight % | | |
|---|---|---|---|
| Ingredients | A | B | C |
| Ethanol | QS 100 | QS 100 | QS 100 |
| Copolymer of Example VI[1] | 0.75 | 1.00 | 1.25 |
| Fragrance | 0.10 | 0.20 | 0.30 |

[1]Alternatively, tonic compositions are prepared using the copolymers of Examples, V, VIII, XXII, XXIII, XXIV, and XXVI.

These products are prepared by dissolving the polymer in the ethanol with stirring and then adding the fragrance and any colors.

These hair tonics are useful for application to the hair to provide a styling and holding benefit.

Example XIV
Hair Conditioner

A hair conditioner composition is prepared from the following components utilizing conventional mixing techniques.

| Ingredient | Weight % |
|---|---|
| Styling Agent Premix | |
| Copolymer of Example IX | 1.00 |
| Silicone Premix | |
| Silicone gum, GE SE76[1] | 0.30 |
| Octamethyl cyclotetrasiloxane | 1.70 |
| Main Mix | |
| Water | QS 100 |
| Cetyl Alcohol | 1.00 |
| Quaternium 18[2] | 0.85 |
| Stearyl Alcohol | 0.70 |
| Hydroxethyl cellulose | 0.50 |
| Ceteareth-20 | 0.35 |
| Fragrance | 0.20 |
| Dimethicone copolyol | 0.20 |
| Citric Acid | 0.13 |
| Methylchloroisothiazolinone (and) | |

-continued

| Ingredient | Weight % |
| --- | --- |
| methylisothiazolinone | 0.04 |
| Sodium Chloride | 0.01 |

[1] Commercially available from General Electric.
[2] Dimethyl Di(Hydrogenated Tallow) Ammonium Chloride The product is prepared by comixing all the Main Mix ingredients, heating to about 60° C. with mixing, and colloid milling while cooling to about 45° C. At this temperature, the two premixies are add separately with moderate agitation and the resultatn conditioner is allowed to cool to room temperature.

This product is useful as a rinse off hair conditioner.

Example XV
Shampoo Composition

A shampoo composition is prepared from the following components utilizing conventional mixing techniques.

| Ingredients | Weight % |
| --- | --- |
| Styling Agent | |
| Copolymer from Example IX | 1.00 |
| Premix | |
| Silicone gum | 0.50 |
| Dimethicone, 350 cs fluid | 0.50 |
| Main Mix | |
| Water | QS 100 |
| Ammonium lauryl sulfate | 11.00 |
| Cocamide MEA | 2.00 |
| Ethylene glycol distearate | 1.00 |
| Xanthan Gum | 1.20 |
| Methylchloroisothiazolinone (and) methylisothiazolinone | 0.04 |
| Citric Acid to pH 4.5 as needed | |

The Main Mix is prepared by first dissolving the xanthan gum in the water with conventional mixing. The remaining Main Mix ingredients are added and the Main Mix is heated to 150° F. with agitation for ½ hour. The Styling Agent and the Premix are then added sequentially with about 10 minutes of agitation between additions, and the entire mixture is stirred while the batch is cooled to room temperature. For varied particile size, the Styling AGent and Premix can be added at different times using either or both high shear mixing (high speed dispersator) or normal agitation.

This shampoos is useful for cleansing the hear and for providing a styling benefit.

Example XVI
Anti-Acne Composition

An anti-acne composition is made by combining the following components using conventional mixing technology.

| Ingredient | Weight % |
| --- | --- |
| Water | QS 100 |
| Salicylic Acid | 2.0 |
| Copolymer from Example VI[1] | 2.0 |
| Ethanol (SDA 40) | 40.0 |

[1] Alternatively, the anti-acne compositions are prepared using the copolymers of Examples VIII, IX, XXII, XXIII, XXIV, and XXVI.

The compositon display skin penetration of the salicylic acid as well as improved skin reel and residue characteristics and is useful for the treatment of acne.

Example XVII
Topical Analgesic Composition

A topical analagesic composition is made by combining the following ingredients utilizing conventional mixing techniques.

| Ingredient | Weight % |
| --- | --- |
| Water, Purified | QS 100 |
| Ibuprofen | 2.0 |
| Copolymer from Example VI[1] | 2.0 |
| Ethanol (SDA 40) | 20.0 |

[1] Alternatively, the topical analagesic compositions are prepared using the copolymers of Examples VIII, IX, XXII, XXIII, XXIV, and XXVI.

The compositions display skin penetration of the ibuprofen active as well as improved skin feel and residue characteristics together with excellent moisturizing, emolliency, rub-in and absorption characteristics.

Example XVIII
Sunless Tanning Composition

A composition for sunless tanning is made by combining the following ingredients utilizing conventional mixing techniques.

| Ingredients | Weight % |
| --- | --- |
| Phase A | |
| Water | qs 100 |
| Copolymer from Example VI[1] | 2.00 |
| Carbomer 934[2] | 0.20 |
| Carbomer 980[3] | 0.15 |
| Acrylic Acid Copolymer[4] | 0.15 |
| Phase B | |
| PPG-20 Methyl Glucose Ether Distearate | 2.00 |
| Tocopheryl Acetate | 1.20 |
| Mineral Oil | 2.00 |
| Stearyl Alcohol | 1.00 |
| Shea Butter | 1.00 |
| Cetyl Alcohol | 1.00 |
| Ceteareth-20 | 2.50 |
| Ceteth-2 | 1.00 |
| Ceteth-10 | 1.00 |
| Phase C | |
| DEA-Cetyl Phosphate | 0.75 |
| Phase D | |
| Dihydroxyacetone | 3.00 |
| Phase E | |
| Butylene Glycol | 2.00 |
| DMDM Hydantoin (and) Iodopropynyl Butylcarbamate | 0.25 |
| Phase F | |
| Fragrance | 1.00 |
| Cyclomethicone | 2.00 |

[1] Alternatively, the artificial tanning compositions are prepared using the copolymers of Examples VIII and IX.
[2] Available as Carbopol ® 934 from B. F. Goodrich.
[3] Available as Carbopol ® 980 from B. F. Goodrich.
[4] Available as Pemulen TR1 from B. F. Goodrich.

In a suitable vessel the Phase A ingredients are dispersed in the water and heated to 75–85° C. In a separate vessel the Phase B ingredients are combined and heated to 85–90° C. until melted. Next, the DEA-Cetyl Phosphate is added to the liquid Phase B and stirred until dissolved. This mixture is then added to Phase A to form the emulsion. The emulsion is cooled to 40–45° C. with continued mixing. Next, in a separate vessel, the dihydroxyacetone is dissolved in water and the resulting solution is mixed into the emulsion. In another vessel, the Phase E ingredients are heated with mixing to 40–45° C. until a clear solution is formed and this solution is then added to the emulsion. Finally, the Phase F ingredients are added to the emulsion with mixing, which is then cooled to 30–35° C., and then to room temperature.

This emulsion is useful for topical application to the skin to provide an artificial tan.

Example XIX
Sunscreen Composition

An oil-in-water emulsion is prepared by combining the following components utilizing conventional mixing techniques.

| Ingredients | Weight % |
|---|---|
| Phase A | |
| Water | QS 100 |
| Carbomer 954[1] | 0.24 |
| Carbomer 1342[2] | 0.16 |
| Copolymer from Example VI[3] | 1.75 |
| Disodium EDTA | 0.05 |
| Phase B | |
| Isoarachidyl Neopentanoate[4] | 2.00 |
| PVP Eicosene Copolymer[5] | 2.00 |
| Octyl Methoxycinnamate | 7.50 |
| Octocrylene | 4.00 |
| Oxybenzone | 1.00 |
| Titanium Dioxide | 2.00 |
| Cetyl Palmitate | 0.75 |
| Stearoxytrimethylsilane (and) Stearyl Alcohol[6] | 0.50 |
| Glyceryl Tribehenate[7] | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate[8] | 0.25 |
| dL Panthenol | 1.00 |
| Phase E | |
| Cyclomethicone | 1.00 |

[1]Available as Carbopol ® 954 from B. F. Goodrich.
[2]Available as Carbopol ® 1342 from B. F. Goodrich.
[3]Alternatively, the sunscreen compositions are prepared using the copolymers of Examples VIII and IX.
[4]Available as Elefac I-205 from Bernel Chemical.
[5]Available as Ganex V-220 from GAF Corporation.
[6]Available as DC 580 Wax from Dow Corning.
[7]Available as Synchrowax HRC from Croda.
[8]Available as Glydant Plus from Lonza.

In a suitable vessel the Phase A ingredients are dispersed in the water and heated to 75–85° C. In a separate vessel the Phase B ingredients (except DEA-Cetyl Phosphate) are combined and heated to 85–90° C. until melted. Next, the DEA-Cetyl Phosphate is added to the liquid Phase B and stirred until dissolved. This mixture is then added to Phase A to form the emulsion. The Phase C ingredients are combined until dissolved and then added to the emulsion. The emulsion is then cooled to 40–45° C. with continued mixing. In another vessel, the Phase D ingredients are heated with mixing to 40–45° C. until a clear solution is formed and this solution is then added to the emulsion. Finally, the emulsion is cooled to 35° C. and the Phase E ingredient is added and mixed.

This emulsion is useful for topical application to the skin to provide protection from the harmful effects of ultraviolet radiation.

Example XX
Facial Moisturizer

A leave-on facial emulsion composition containing a cationic hydrophobic surfactant is prepared by combining the following components utilizing conventional mixing techniques.

| Ingredient | Weight % |
|---|---|
| Water | QS 100 |
| Copolymer from Example VI[1] | 1.00 |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Octyldodecyl Myristate | 0.20 |
| Carbomer 1342 | 0.125 |
| Tetrasodium EDTA | 0.10 |
| DMDM Hydantoin and Iodopropynyl Butyl Carbamate | 0.10 |
| Carbomer 951 | 0.075 |

[1]Alternatively, the moisturizers are prepared using the copolymers of Examples VIII, IX, XXII, XXIII, XXIV, and XXVI.

This emulsion is useful for application to the skin as a moisturizer.

Example XXI
Styryl Capped Poly(2-vinyl pyridine) Macromonomer

Approximately 800 mL of dry tetrahydrofuran is placed in a round bottom flask equipped with a mechanical stirrer and a thermometer and is cooled to −78° C. using a dry ice/isopropanol bath. Next 7.69 grams (0.01 mole) of sec-butyl lithium (1.3 Molar solution in hexane) and 1.89 grams (0.0124 mole) of diphenylethylene are added. The mixture is then allowed to stir for 5 minutes. Next, 2-vinyl pyridine (105 grams, 1.0 moles) is added dropwise with stirring. After the addition is complete, 2.29 grams (0.15 mole) of para-vinyl benzyl chloride is added, and the reaction mixture is allowed to warm to room temperature with stirring. The reaction product is then carefully poured into 1 liter of n-hexames solvent to precipitate the macromonomer. The macromonomer is isolated by suction filtration followed by drying under vacuum to yield 97.0 grams (92% yield) of styryl capped poly(2-vinyl pyridine) macromonomer.

Using the above procedure, the following monomers are used to prepare their corresponding macromonomers: 3-vinylpyridine, 4-vinylpyridine, 4-vinyl aminomethylbenzene, 4-vinyl dimethylaminomethylbenzene, 2-vinyl-5-chloropyridine, 2-vinyl4-methylpyridine, and 4-vinyl dimethylaminoethylbenznen.

Example XXII
Synthesis Of Poly(n-Butyl Acrylate-Co-2-Methoxyethylacrylate)-Graft-Poly(2-Vinylpyridine)

To a solution of 16.0 g (0.1248 mol) of n-butyl acrylate, and 4 g of styryl capped poly(2-vinyl pyridine) macromonomer (from Example XI) in 100 mL of acetone is added 0.03 g (0.00018 mol) of azoisobutyronitrile (AIBN) initiator. The resulting solution is refluxed slowly for about 20 hours. The reaction is then quenched by the addition of about 5 mL of methanol. The solution is then poured into a teflon pan and the acetone is evaporated at room temperature under a fume hood. The resulting polymer film is redissovled in ethanol, filtered, and the ethanol is then evaporated to yield about 18.4 g of the thermoplastic elastomeric copolymer.

Alternatively, by varying the monomers and macromoners used, this procedure is used to prepare other copolymers of the present invention.

Example XXIII
Synthesis Of Methyl Quaternized Polymer Of Example XII

To 5 grams of the copolymer from example XXII dissolved in 80 grams of ethanol is added dropwise 2.16 grams (0.0140 mole) of dimethylsulfate. The resulting solution is stirred for 2 hours at room temperature. The solvent is removed by rotary evaporation to yield the methyl quaternized copolymer.

Example XXIV
Synthesis Of Hydrochloride Salt Of Polymer Of Example XXII

To 5 grams of the copolymer from Example XXII dissolved in 80 grams of ethanol is bubbled in hydrogen chloride gas for approximately 15 minutes. The solvent is removed by rotary evaporation to yield the hydrochloride salt of the copolymer.

Example XXV
Styryl Capped Poly(N,N-Dimethylacrylamide)

Using the procedure of Example XXI, 99 grams, (1.0 mole) of N,N-dimethylacrylamide is used instead of 2-vinylpyridine.

In an alternative procedure, the corresponding styryl capped poly(N,N-dimethylmethylacrylamide) is prepared using N,N-dimethylmethacrylamide.

Example XXVI
Synthesis Of Poly(n-Butyl Acrylate-Co-2-Methoxyethylacrylate)-Graft-[Poly(2-N,N-Dimethylacrylamide)

Using the method of Example XXII, 4.0 grams of styryl capped poly(N,N-dimethylacrylamide) is used to replace the styryl capped poly(2-vinylpyridine).

What is claimed is:

1. A water or alcohol soluble or dispersible thermoplastic elastomeric copolymer having a backbone and two or more polymeric side chains, said copolymer formed from the copolymerization of randomly repeating A and B units wherein said copolymer comprises:
   (i) from about 40% to about 90% by weight of said A units, wherein said A units are polymerizable monomer units; and
   (ii) from about 10% to about 60% by weight of said B units, wherein said B units are hydrophilic macromonomer units, copolymerizable with A, whereby said macromonomer units form said polymeric side chains; and wherein said B macromonomer units are selected from nitrogen containing macromonomers represented by the following structure

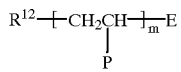

wherein $R^{12}$ is selected from the group consisting of hydrogen, $C_1$–$C_6$ straight or branched chain alkyl, benzyl, and mixtures thereof m is an integer from about 10 to about 2000; E is an etheneically unsaturated moiety, copolymerizable with A, selected from the group consisting of vinyl, allyl, acryloyl, methacryloyl, ethacryloyl, styryl, 2-vinyl benzyl, 3-vinyl benzyl, 4-vinyl benzyl, 2-vinylbenzoyl, 3-vinylbenzoyl, 4-vinylbenzoyl, 1-butenyl, isobutenyl, isoprenyl, cyclopentenyl, cyclohexenyl, and mixtures thereof; and P is selected from the group consisting of pharmaceutically acceptable salts or $C_1$–$C_{30}$ straight or branched chain alkyl quaternized derivatives of 2-pyridyl, 3-pyridyl, 4-pyridyl, 4-dimethylaminomethyl benzene, 4-aminomethyl benzene, 4-dimethylaminoethyl benzene, 4-aminoethyl benzene, and mixtures thereof;

wherein said copolymer has a weight average molecular weight greater than about 10,000, and wherein said copolymer exhibits two distinct $T_g$ values, said first $T_g$ corresponding to said backbone and having a value less than about 0° C., and said second $T_g$ corresponding to said polymeric side chains and having a value greater than about 25° C.

2. A copolymer according to claim 1 wherein $R^{12}$ is 1,1-diphenyl-4-methylpentyl and m is an integer from about 20 to about 250.

3. A copolymer according to claim 2 wherein P is selected from the group consisting of hydrochloride and hydrobromide salts of 2-pyridyl, 3-pyridyl, 4-pyridyl, methyl and ethyl quaternized derivatives of 2-pyridyl, 3-pyridyl, 4-pyridyl, and mixtures thereof.

4. A copolymer according to claim 2 wherein P is methyl quaternized 2-pyridyl.

5. A copolymer according to claim 4 wherein the $T_g$ corresponding to said backbone is from about –45° C. to about –120° C., and the $T_g$ corresponding to said hydrophilic polymeric side chains is from about 35° C. to about 150° C.

6. A copolymer according to claim 4 wherein said A monomer units comprise from about 50% to about 85% by weight of the total copolymer and said B macromonomer units comprise from about 15% to about 50% by weight of the total copolymer.

7. A copolymer according to claim 6 wherein said A monomer units comprise from about 60% to about 80% by weight of the total copolymer and said B macromonomer units comprise from about 20% to about 40% by weight of the total copolymer.

8. A copolymer according to claim 7 wherein said A monomer units are of the formula

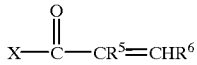

wherein X is selected from the group consisting of —OH, —OM, —OR$^4$, —NH$_2$, —NHR$^4$, and —N(R$^4$)$_2$; M is a cation selected from the group consisting of Na+, K+, Mg++, Ca++, Zn++, NH$_4$+, alkylammonium, dialkylammonium, trialkylammonium, and tetralkylammonium; R$^4$ is selected from the group consisting of H, $C_1$–$C_8$ straight or branched chain alkyl, N,N-dimethylaminoethyl, methyl quaternized N,N-dimethylaminoethyl, 2-hydroxyethyl, 2-methoxyethyl, and 2-ethoxyethyl; and R$^5$ and R$^6$ are independently selected from the group consisting of H, $C_1$–$C_8$ straight or branched chain alkyl, methoxy, ethoxy, 2-hydroxyethyl, 2-methoxyethyl, and 2ethoxyethyl.

9. A copolymer according to claim 8 wherein said A monomer units are selected from the group consisting of n-butyl acrylate, 2-ethylhexyl acrylate, N-octyl acrylamide, 2-methoxyethyl acrylate, 2-hydroxyethyl acrylate, N,N- dimethylaminoethyl acrylate, methyl quaternized N,N-dimethylaminoethyl acrylate, and mixtures thereof.

10. A water or alcohol soluble or dispersible thermoplastic elastomeric copolymer having a backbone and one or more polymeric side chains, said copolymer formed from the copolymerization of randomly repeating A and B units and corresponding to the formula $$[A]_a[B]_b$$

wherein (i) A is at least one polymerizable monomer unit corresponding to the formula

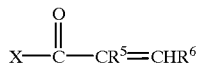

wherein X is selected from the group consisting of —OH, —OM, —OR$^4$, —NH$_2$, —NHR$^4$, and —N(R$^4$)$_2$; M is a cation selected from the group consisting of Na+, K+, Mg++, Ca++, Zn++, NH$_4$+, alkylammonium, dialkylammonium, triallylammonium, and tetralkylammonium; each R$^4$ is selected from the group consisting of H, C$_1$–C$_8$ straight or branched chain allyl, N,N,-dimethylaminoethyl, 2-hydroxyethyl, 2-methoxyethyl, and 2-ethoxyethyl; and R$^5$ and R$^6$ are independently selected from the group consisting of H, C$_1$–C$_8$ straight or branched chain alkyl, methoxy, ethoxy, 2-hydroxyethoxy, 2-methoxyethyl, and 2-ethoxyethyl;

(ii) B is at least one hydrophilic nitrogen containing macromonomer unit copolymerizable with A corresponding to the formula

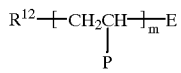

wherein R$^{12}$ is selected from the group consisting of hydrogen, C$_1$–C$_6$ straight or branched chain allyl benzyl, and mixtures thereof m is an integer from about 10 to about 2000; E is an ethylenically unsaturated moiety, copolymerizble with A and C, selected from the group consisting of vinyl, allyl, acryloyl, methacryloyl, ethacryloyl, styryl, 2-vinyl benzyl, 3-vinyl benzyl, 4-vinyl benzyl, 2-vinylbenzoyl, 3-vinylbenzoyl, 4-vinylbenzoyl, 1-butenyl, isobutenyl, isoprenyl, cyclopentyl, cyclohexenyl, and mixtures thereof, and P is selected from the group consisting of pharmaceutically acceptable salts and C$_1$–C$_{30}$ straight or branched chain alkyl quaternized derivatives of 2-pyridyl, 3-pyridyl, 4-pyridyl, 4-dimethylaminoethyl benzene, 4-aminoethyl benzene, 4-dimethylaminoethyl benzene, 4-aminoethyl benzene, and mixtures thereof;

(iii) a is an integer of about 100 or greater and b is an integer of about 2 or greater; and wherein said copolymer exhibits two distinct T$_g$ values, said first T$_g$ corresponding to said backbone and having a value less than about 0° C., and said second T$_g$ corresponding to said polymeric side chains and having a value greater than about 25° C.

11. A copolymer according to claim 10 wherein said A monomer units are selected from the group consisting of n-butyl acrylate, 2-ethylhexyl acrylate, N-octyl acrylamide, 2-methoxyethyl acrylate, 2-hydroxyethyl acrylate, N,N-dimethylaminoethyl acrylate, and mixtures thereof; R is methyl, R' is ethyl, m is an integer from about 10 to about 2000, a is an integer from about 100 to about 3000, and b is an integer from about 2 to about 50.

12. A hair care composition useful for styling hair, comprising the copolymer of claim 1 and a carrier suitable for application to the hair.

13. A hair care composition according to claim 12, in the form of a liquid suitable for application to the hair, wherein said carrier comprises water, a C1–C6 monohydric alcohol, or a mixture thereof.

14. A hair care composition according to claim 13 which further comprises a propellant.

15. A hair care composition according to claim 12, in the form of a liquid suitable for application to the hair, wherein said carrier comprises a solvent selected from the group consisting of water, methanol, ethanol, isopropanol, and mixtures thereof.

16. A hair care composition according to claim 12, in the form of a mousse for application to the hair, wherein said carrier comprises water, one or more surfactants, and a propellant.

17. A composition for topical application to the skin comprising the copolymer of claim 1 and a carrier suitable for application to the skin.

18. A water or alcohol soluble or dispersible thermoplastic elastomeric copolymer having a backbone and two or more polymeric side chains, said copolymer formed from the copolymerization of randomly repeating A and B units wherein said copolymer comprises:

(i) from about 50% to about 85% by weight of said A units, wherein said A units are polymerizable monomer units; and said A monomer units are of the formula

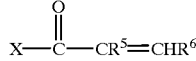

wherein X is selected from the group consisting of —OH, —OM, —OR$^4$, —NH$_2$, —NHR$^4$, AND —N(R$^4$)$_2$; M is a cation selected from the group consisting of Na+, K+, Mg$^2$++, Ca++, Zn++, NH$_4$+, alkylammonium, dialkylammonium, trialkylammonium, and tetralkylammonium; R$^4$ is selected from the group consisting of H, C$_1$–C$_8$ straight or branched chain alkyl, N,N-dimethylaminoethyl, methyl quaternized N,N-dimethylaminoethyl, 2-hydroxyethyl, 2-methoxyethyl, and 2-ethoxyethyl; and R$^5$ and R$^6$ are independently selected from the group consisting of H, C$_1$–C$_8$ straight or branched chain alkyl, methoxy, ethoxy, 2-hydroxyethyl, 2-methoxyethyl, and 2-ethoxyethyl; and (ii) from about 15% to about 50% by weight of said B units, wherein said B units are hydrophllic macromonomer units, copolymerizable with A, whereby said macromonomer units form said polymeric side chains; and wherein said B macromonomer units are selected from nitrogen containing macromonomers represented by the following structure

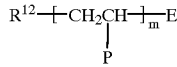

where in R$^{12}$ is selected from the group consisting of hydrogen, C$_1$–C$_6$ straight or branched chain alkyl, benzyl, and mixtures thereof, m is an integer from about 10 to about 2000;

E is an ethylenically unsaturated moiety, copolymerizable with A, selected from the group consisting of vinyl, allyl, acryloyl, methacryloyl, ethacryloyl syl, 2-vinyl benzyl, 3-vinyl benzyl, 4-vinyl benzyl, 2-vinylbenzoyl, 3-vinylbenzoyl, 4-vinylbenzoyl, 1-butenyl, isobutenyl, isoprenyl, cyclopentenyl, cyclohexenyl, and mixtures thereof; and P is selected from the g roup consisting of hyd rochloride and hydrobromide salts of 2-pyridyl, 3-pyridyl, 4-pyridyl, methyl and ethyl quaternized derivatives of 2-pyridyl 3-pyridyl, 4-pyridyl, and mixtures thereof;

wherein said copolymer has a weight average molecular weight greater than about 10,000, and wherein said copolymer exhibits two distinct $T_g$ values, said first $T_g$ corresponding to said backbone and having a value from about $-20°$ C. to about $-125°$ C., and said second $T_g$ corresponding to said polymeric side chains and having a value greater than about $25°$ C.

* * * * *